(12) United States Patent
Huang et al.

(10) Patent No.: US 11,364,275 B2
(45) Date of Patent: Jun. 21, 2022

(54) LINEAR LIPOPEPTIDE PAENIPEPTINS AND METHODS OF USING THE SAME

(71) Applicant: BioVentures, LLC, Little Rock, AR (US)

(72) Inventors: En Huang, Little Rock, AR (US); Sun Hee Moon, Little Rock, AR (US); Mark Smeltzer, Little Rock, AR (US); Daniel Meeker, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 0 days.

(21) Appl. No.: 16/635,748

(22) PCT Filed: Aug. 6, 2018

(86) PCT No.: PCT/US2018/045395
§ 371 (c)(1),
(2) Date: Jan. 31, 2020

(87) PCT Pub. No.: WO2019/028463
PCT Pub. Date: Feb. 7, 2019

(65) Prior Publication Data
US 2021/0128669 A1    May 6, 2021

Related U.S. Application Data

(60) Provisional application No. 62/541,200, filed on Aug. 4, 2017.

(51) Int. Cl.
*A61K 38/08* (2019.01)
*A61K 45/06* (2006.01)

(52) U.S. Cl.
CPC ............. *A61K 38/08* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,294,754 A * | 10/1981 | Takahara | A61P 31/04 530/332 |
| 7,375,081 B2 | 5/2008 | Ikeda | |
| 8,415,307 B1 | 4/2013 | Curran | |
| 2013/0174298 A1 | 7/2013 | Christensen | |

FOREIGN PATENT DOCUMENTS

| | | | |
|---|---|---|---|
| WO | 2000012541 A2 | 3/2000 | |
| WO | 2001021596 A1 | 3/2001 | |
| WO | WO-2006110182 A2 * | 10/2006 | ............... C12N 9/93 |

OTHER PUBLICATIONS

Huang, En et al, "New paenibacillus strain produces a family of linear and cyclic antimicroial lipopeptides: cyclization is not essential for their antimicrobial activity." FEMS Microbiol. Lett. (Feb. 2017) 364 fnx049.*
Yampolsky, Lev Y. and Stoltzfus, Arlin; "The exchangeability of amino acids in proteins." Genetics (2005) 170 p. 1459-1472.*
Maraj, Rajiv et al.; "Evaluation of hemolysis in patients with prosthetic heart valves." Clin. Cardiol. (1998) 21 p. 387-392.*
Kato, Soulchiro et al; "Isolation of previously uncultured slow growing bacteria by using a simple modification in the preparation of agar media." Appl. Environ. Microbiol. (2018) 84e00807-18.*
The entry for cyclohexylalanine in Drugbank, go.drugbank.com/drugs/DB02884, downloaded Sep. 21, 2021.*
Beenken, K. E., et al. (2003). Mutation of sarA in *Staphylococcus aureus* limits biofilm formation. Infection and immunity, 71(7), 4206-4211.
Benge GR. 1988. Bactericidal activity of human serum against strains of Klebsiella from different sources. J Med Microbiol 27: 11-15.
Cochrane, S. A., et al. (2014). Synthesis and structure-activity relationship studies of N-terminal analogues of the antimicrobial peptide tridecaptin A1. Journal of medicinal chemistry, 57(3), 1127-1131.
Cochrane, S. A.; et al. Unacylated tridecaptin A 1 acts as an effective sensitiser of Gram-negative bacteria to other antibiotics. International journal of antimicrobial agents 2014, 44, 493-499.
Craig, W. A.; et al. In vivo pharmacodynamics of new lipopeptide MX-2401. Antimicrob. Agents Chemother. 2010, 54, 5092-5098.
De Zoysa, G. H., et al. (2015). Antimicrobial peptides with potential for biofilm eradication: synthesis and structure activity relationship studies of battacin peptides. Journal of medicinal chemistry, 58(2), 625-639.
Deleo FR, et al. 2017. Survival of carbapenem-resistant Klebsiella pneumoniae sequence type 258 in human blood. Antimicrob Agents Chemother 61: e02533-16.
Ding, R., et al. "Isolation and identification of lipopeptide antibiotics from Paenibacillus elgii B69 with inhibitory activity against methicillin-resistant *Staphylococcus aureus*." The Journal of Microbiology 49.6 (2011): 942-949.
Fischbach, M. A., et al. (2009). Antibiotics for emerging pathogens. Science, 325(5944), 1089-1093.
Flemming, H. C., et al. (2016). Biofilms: an emergent form of bacterial life. Nature Reviews Microbiology, 14(9), 563-575.
Garrison, M. W.; et al. Assessment of effects of protein binding on daptomycin and vancomycin killing of *Staphylococcus aureus* by using an in vitro pharmacodynamic model. Antimicrob. Agents Chemother. 1990, 34, 1925-1931.
Huang E. et al. 2014. Paenibacterin, a novel broad-spectrum lipopeptide antibiotic, neutralises endotoxins and promotes survival in a murine model of Pseudomonas aeruginosa induced sepsis. Int J Antimicrob Agents 44: 74-77.

(Continued)

*Primary Examiner* — Fred H Reynolds
(74) *Attorney, Agent, or Firm* — Quarles & Brady, LLP

(57) ABSTRACT

Disclosed herein are linear lipopeptides having antimicrobial and antibiofilm activity. In one aspect of the invention the linear lipopeptide comprising a lipophilic terminus, an amine terminus, and a peptide interposed between the lipophilic terminus and the amine terminus or a salt thereof. The peptide may comprise any of SEQ ID Nos: 1-17 or a derivative thereof. Products comprising the lipopeptides and methods of using the same are also disclosed.

11 Claims, 7 Drawing Sheets

Specification includes a Sequence Listing.

(56) References Cited

OTHER PUBLICATIONS

Huang E. et al. New Paenibacillus strain produces a family of linear and cyclic antimicrobial lipopeptides: cyclization is not essential for their antimicrobial activity. FEMS Microbiology Letters 2017, 364.
Huang E. et al. (2014). The lipopeptide antibiotic paenibacterin binds to the bacterial outer membrane and exerts bactericidal activity through cytoplasmic membrane damage. Applied and environmental microbiology, 80(9), 2700-2704.
International Searching Authority. International Search Report and Written Opinion for application PCT/US2018/045395, dated Dec. 4, 2018.
Jammal, J., et al. (2015). Sensitization of Gram-negative bacteria to rifampin and OAK combinations. Scientific reports, 5.
Katsuma, N., et al. (2009). Development of des-fatty acyl-polymyxin B decapeptide analogs with Pseudomonas aeruginosa-specific antimicrobial activity. Chemical and Pharmaceutical Bulletin, 57(4), 332-336.
Liu, Y. Y., et al. (2016). Emergence of plasmid-mediated colistin resistance mechanism MCR-1 in animals and human beings in China: a microbiological and molecular biological study. The Lancet Infectious Diseases, 16(2), 161-168.
Meeker, D. G., et al. (2016). Evaluation of antibiotics active against methicillin-resistant *Staphylococcus aureus* based on activity in an established biofilm. Antimicrobial Agents and Chemotherapy, 60(10), 5688-5694.
Moon, S. H., et al. "Lipopeptide paenipeptin analogues potentiate clarithromycin and rifampin against carbapenem-resistant pathogens." Antimicrobial Agents and Chemotherapy 62.8 (2018).
Moon, S. H., et al. "Novel linear lipopeptide paenipeptins with potential for eradicating biofilms and sensitizing Gram-negative bacteria to rifampicin and clarithromycin " Journal of medicinal chemistry 60.23 (2017): 9630-9640.
Qian, C-D, et al. "Identification and functional analysis of gene cluster involvement in biosynthesis of the cyclic lipopeptide antibiotic pelgipeptin produced by Paenibacillus elgii." BMC microbiology 12.1 (2012): 197.
Sato, Y., et al. (2011). Novel des-fatty acyl-polymyxin B derivatives with Pseudomonas aeruginosa-specific antimicrobial activity. Chemical and Pharmaceutical Bulletin, 59(5), 597-602.
Sugawara, K., et al. "BMY-28160, a new peptide antibiotic." The Journal of antibiotics 37.10 (1984): 1257-1259.
Takeuchi, Y., et al. "The structure of permetin A, a new polypeptin type antibiotic produced by Bacillus circulans." The Journal of antibiotics 32.2 (1979): 121-129.
Tsubery, H., et al. (2001). N-terminal modifications of polymyxin B nonapeptide and their effect on antibacterial activity. Peptides, 22(10), 1675-1681.
Vaara, M. (1992). Agents that increase the permeability of the outer membrane. Microbiological reviews, 56(3), 395-411.
Vaara, M. et al. A novel polymyxin derivative that lacks the fatty acid tail and carries only three positive charges has strong synergism with agents excluded by the intact outer membrane. Antimicrobial agents and chemotherapy 2010, 54, 3341-3346.
Vaara, M. et al. Novel polymyxin derivatives carrying only three positive charges are effective antibacterial agents. Antimicrobial agents and chemotherapy 2008, 52, 3229-3236.
Velkov, T et al. Structure-activity relationships of polymyxin antibiotics. Journal of medicinal chemistry 2009, 53, 1898-1916.
Wirker, M.A. Methods for Dilution Antimicrobial Susceptibility Tests for Bacteria that Grow Aerobically: Approved Standard M07-A8; Clinical and Laboratory Standards Institute, Wayne, PA, 2009.
Wu, X-C, et al. "Isolation and partial characterization of antibiotics produced by Paenibacillus elgii B69." FEMS microbiology letters 310.1 (2010): 32-38.
Yang, X. et al. Brevibacillin, a cationic lipopeptide that binds to lipoteichoic acid and subsequently disrupts cytoplasmic membrane of *Staphylococcus aureus*. Microbiol. Res., 2017, 195, 18-23.
Zabawa, T. P. et al. Treatment of Gram-negative bacterial infections by potentiation of antibiotics. Current opinion in microbiology 2016, 33, 7-12.

* cited by examiner

SEQUENCE LISTING

```
<160> NUMBER OF SEQ ID NOS: 17

<210> SEQ ID NO 1
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Val is dVal

<400> SEQUENCE: 1

Xaa Ile Xaa Phe Leu Xaa Val Leu Ser
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Val is dVal

<400> SEQUENCE: 2

Xaa Val Xaa Phe Leu Xaa Val Leu Ser
1               5
```

```
<210> SEQ ID NO 3
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Val is dVal

<400> SEQUENCE: 3

Xaa Phe Xaa Phe Leu Xaa Val Leu Ser
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Leu is dLeu

<400> SEQUENCE: 4

Xaa Ile Xaa Phe Leu Xaa Leu Leu Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Leu is dLeu

<400> SEQUENCE: 5

Xaa Phe Xaa Phe Leu Xaa Leu Leu Ser
1               5

<210> SEQ ID NO 6
```

```
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Leu is dLeu

<400> SEQUENCE: 6

Xaa Phe Xaa Phe Leu Xaa Leu Phe Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3, 6 and 9 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Val is dVal

<400> SEQUENCE: 7

Xaa Ile Xaa Phe Leu Xaa Val Leu Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 2, 3, 6 and 9 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Val is dVal

<400> SEQUENCE: 8

Xaa Xaa Xaa Phe Leu Xaa Val Leu Xaa
1               5

<210> SEQ ID NO 9
<211> LENGTH: 9
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at 1, 3, and 6 is ornithine
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Val is dVal

<400> SEQUENCE: 9

Xaa Ile Xaa Phe Leu Xaa Val Leu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1 and 6 is 2,4-
      diaminobutyric acid
<220> FEATURE:
<221> NAME/KEY: misc_feature
<222> LOCATION: (4)..(4)
<223> OTHER INFORMATION: Leu is dLeu
<220> FEATURE:
<221> NAME/KEY: misc_feature
<222> LOCATION: (7)..(7)
<223> OTHER INFORMATION: Val is dVal

<400> SEQUENCE: 10

Xaa Ile Thr Leu Leu Xaa Val Leu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Val is dVal

<400> SEQUENCE: 11

Xaa Ile Xaa Phe Leu Xaa Val Leu Ser
1               5

<210> SEQ ID NO 12
<211> LENGTH: 9
<212> TYPE: PRT
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (2)..(2)
<223> OTHER INFORMATION: Xaa is 4-phenyl-phenylalanyl
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Val is dVal

<400> SEQUENCE: 12

Xaa Xaa Xaa Phe Leu Xaa Val Leu Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Xaa is 4-phenyl-phenylalanyl
<220> FEATURE:
<221> NAME/KEY: misc_feature
<222> LOCATION: (7)..(7)
<223> OTHER INFORMATION: Val is dVal

<400> SEQUENCE: 13

Xaa Ile Xaa Xaa Leu Xaa Val Leu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (5)..(5)
<223> OTHER INFORMATION: Xaa is 4-phenyl-phenylalanyl
<220> FEATURE:
<221> NAME/KEY: misc_feature
<222> LOCATION: (7)..(7)
<223> OTHER INFORMATION: Val is dVal

<400> SEQUENCE: 14

Xaa Ile Xaa Phe Xaa Xaa Val Leu Ser
```

```
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Xaa is 4-phenyl-phenylalanyl

<400> SEQUENCE: 15

Xaa Ile Xaa Phe Leu Xaa Xaa Leu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Val is dVal
<220> FEATURE:
<221> NAME/KEY: misc_feature
<222> LOCATION: (8)..(8)
<223> OTHER INFORMATION: Xaa is 4-phenyl-phenylalanyl

<400> SEQUENCE: 16

Xaa Ile Xaa Phe Leu Xaa Val Xaa Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa at positions 1, 3 and 6 is 2,4-
      diaminobutyric acid
<220> FEATURE:
<221> NAME/KEY: misc_feature
<222> LOCATION: (4)..(4)
<223> OTHER INFORMATION: Phe is dPhe
<220> FEATURE:
<221> NAME/KEY: misc_feature
<222> LOCATION: (7)..(7)
<223> OTHER INFORMATION: Val is dVal
<220> FEATURE:
```

```
<221> NAME/KEY: misc_feature
<222> LOCATION: (8)..(8)
<223> OTHER INFORMATION: Xaa is Octylglycy

<400> SEQUENCE: 17

Xaa Ile Xaa Phe Leu Xaa Val Xaa Ser
1               5
```

LINEAR LIPOPEPTIDE PAENIPEPTINS AND METHODS OF USING THE SAME

CROSS-REFERENCE TO RELATED APPLICATIONS

This patent application is a national stage filing under 35 U.S.C. 371 of International Application No. PCT/US2018/045395, filed Aug. 6, 2018, which claims the benefit of priority of U.S. Provisional Patent Application No. 62/541,200, filed Aug. 4, 2017, both of which are incorporated herein by reference in their entirety.

FIELD OF INVENTION

The technology disclosed herein is generally directed to linear lipopeptide paenipeptins and methods of using the same as antimicrobials and potentiators.

SEQUENCE LISTING

This application is being filed electronically via EFS-Web and includes an electronically submitted Sequence Listing in .txt format. The .txt file contains a sequence listing entitled "2018-08-06_6401-00035_ST25.txt" created on Aug. 6, 2018 and is 7,960 bytes in size. The Sequence Listing contained in this .txt file is part of the specification and is hereby incorporated by reference herein in its entirety.

BACKGROUND

The continuing emergence and rapid dissemination of antibiotic-resistant pathogens are becoming a major threat to public health. Infections caused by carbapenem-resistant Enterobacteriaceae (CRE), which are difficult to treat and often untreatable, were recognized as one of the urgent threats among patients in medical facilities. Other serious threats caused by drug-resistant pathogens include multidrug-resistant *Acinetobacter*, multidrug-resistant *Pseudomonas aeruginosa*, drug-resistant *Campylobacter*, vancomycin-resistant *Enterococcus*, and methicillin-resistant *Staphylococcus aureus* (CDC, 2013). Recently, the plasmid-mediated polymyxin-resistant gene, mcr-1, from Gram-negative bacteria was reported in many countries all over the world (Liu et al, 2016). These findings implied a major breach of the last line of defense against drug-resistant pathogens. Compounding the concern, many bacterial pathogens are capable of forming biofilms, which are matrix-embedded cell aggregates, intrinsically tolerant to most antibiotic treatment, on both native host tissues and indwelling medical devices (Flemming et al., 2016). Serious infections caused by antibiotic-resistant pathogens are associated with high rates of morbidity and mortality and contribute to significant economic costs. Therefore, there is an urgent need to develop novel, safe, and effective antimicrobial agents for the treatment of infections caused by drug-resistant and biofilm-forming pathogens.

SUMMARY OF THE INVENTION

Disclosed herein are linear lipopeptide paenipeptins, products comprising the lipopeptides, and methods of using the same. One aspect of the invention includes antimicrobial compositions. The antimicrobial composition may comprise a linear lipopeptide, the lipopeptide comprising a peptide having at least 66% sequence identity with any one of SEQ ID NOs: 1-17 interposed between a lipophilic terminus $-R^1$ and an amine terminus $-NR^2R^3$. $R^1$ may comprise a substituted or unsubstituted, branched or unbranched $C_2$-$C_{20}$ alkanoyl and $R^2$ and $R^3$ may be independently selected from hydrogen or a $C_1$-$C_6$ alkyl. Suitably, the composition may possess one or more of the following properties:

(a) the lipopeptide has a minimum inhibitory concentration less than or equal to 8.0 µg/mL against a microbe in a culture medium;

(b) the lipopeptide has a minimum bactericidal concentration less than or equal to 16.0 µg/mL against a microbe in a culture medium;

(c) the lipopeptide has a hemolysis percentage less than or equal to 50.0% at a lipopeptide concentration of 128 µg/mL;

(d) the lipopeptide has a viability percentage greater than or equal to 50.0% at a lipopeptide concentration of 105 µg/mL;

(e) the lipopeptide has a sensitization factor of greater than or equal to 128 for an antimicrobial agent against a microbe; or (f) the composition has an effective amount of the lipopeptide for an antibiofilm activity of at least a 2.0 log reduction in viable microbes on a surface.

Suitably, the composition may possess at least two, three, four, five, or all of the properties selected from (a), (b), (c), (d), (e), or (f).

In some embodiments, the peptide comprises $R^1$—$X^1$—$X^2$—$X^3$—$X^4$—$X^5$—$X^6$—$X^7$—$X^8$—$X^9$—$NR^2R^3$ where:

$X^1$ may be selected from the group consisting of Dab, Orn, Dap, Lys and Arg;

$X^2$ may be selected from the group consisting of Ile, Val, Phe, Dap, and Phephe;

$X^3$ may be selected from the group consisting of Dab, Orn, Dap, Thr, Lys and Arg;

$X^4$ may be selected from the group consisting of dLeu, dPhe, and Phephe;

$X^5$ may be selected from the group consisting of Leu, Phe and Phephe;

$X^6$ may be selected from the group consisting of Dab, Orn, Dap, Lys and Arg;

$X^7$ may be selected from the group consisting of dVal, dLeu, dPhe and Phephe;

$X^8$ may be selected from the group consisting of Leu, Phe, Phephe, and Octgly; and/or $X^9$ may be selected from the group consisting of Ser and Dab.

Suitably, the peptide may have at least 88% sequence identity with any one of SEQ ID NOs: 1-17. In some embodiments, $-R^1$ comprises: $R^4$—C(=O)— or $R^5$—CH(NH$_2$)—C(=O)—. Suitably, $R^4$ may be selected from the group consisting of alkyl, alkenyl, cycloalkyl, phenylalkyl, biphenylalkyl, alkylamine, cycloalkylamine, phenylalkylamine, biphenylalkylamine, alkoxy, cycloalkoxy, phenylalkoxy, or biphenphylalkoxy or $R^5$ may be selected from the group consisting of alkyl, alkenyl, cycloalkyl, phenylalkyl, and biphenylalkyl. In certain embodiments, $R^2$ and $R^3$ are selected from hydrogen.

The compositions described herein may further comprise an antimicrobial agent, such as an antibacterial agent. Suitably, the composition comprising the antimicrobial agent may possess one or more of the following properties:

(a) the antimicrobial agent has a minimum inhibitory concentration against a microbe in the presence of the lipopeptide less than a minimum inhibitory concentration against the microbe in the absence of the lipopeptide in a culture medium;

(b) the antimicrobial agent has a minimum bactericidal concentration against a microbe in the presence of the lipopeptide less than a minimum bactericidal concentration against the microbe in the absence of the lipopeptide in a culture medium;

(c) the lipopeptide has a sensitization factor of greater than or equal to 128 for the antimicrobial agent against a microbe; or (d) the composition has an effective amount of the lipopeptide and/or the antimicrobial agent for an antibiofilm activity of at least a 2.0 log reduction in viable microbes on a surface.

Suitably, the composition may possess at least two, three, or all of the properties selected from (a), (b), (c), or (d). The antimicrobial agent may comprise an antibacterial agent. Exemplary antimicrobial agents include, without limitation, ampicillin, clarithromycin, erythromycin, rifampicin, or vancomycin.

Another aspect of the invention comprises antimicrobial products comprising any of the compositions described herein. One such product is a pharmaceutical composition comprising a therapeutically effective amount of any of the compositions described herein and a pharmaceutically acceptable excipient, a carrier, or a diluent. Another such product is an antibiofilm product comprising an effective amount of any of the compositions described herein formulated for application to a surface. Suitably, the antibiofilm product may be formulated as a spray, an ointment, a gel, a foam, a paste, a hydrogel, or a hydrocolloid. Exemplary surfaces suitable for application of the antibiofilm product include, without limitation, a medical device surface, a medical instrument surface, a medical implant surface, a bandage surface, a wound surface, or skin. The antibiofilm product may comprise a medical device, a medical instrument, a medical implant, or a bandage having any of the compositions described herein disposed thereon. Yet another such product is a bandage comprising a dressing and an effective amount of any of the compositions described herein to treat or prevent a microbial infection or a microbial biofilm on a wound or skin. The dressing may comprise a fabric, a sponge, an alginate, a collagen, a film, a gel sheet, a wound filler, a hydrogel, a hydrocolloid, or a combination thereof.

The antimicrobial compositions are effective in inhibiting the proliferation of, killing of, or sensitizing a microbe. Another aspect of the invention comprises a method for inhibiting the proliferation of, killing of, or sensitizing a microbe. The method may comprise contacting the microbe with an effective amount of any of the compositions described herein or any of the antimicrobial products described herein, including any of the pharmaceutical compositions, antibiofilm products, or bandages described herein.

The antimicrobial compositions are also effective in preventing of the formation of a biofilm on a surface or inhibiting proliferation of, killing of, or sensitizing a microbe in the biofilm. Another aspect of the invention comprises a method for preventing of the formation of a biofilm on a surface or inhibiting proliferation of, killing of, or sensitizing a microbe in the biofilm. The method may comprise contacting the surface or a biofilm disposed thereon with an effective amount of any of the compositions described herein or any of the antimicrobial products described herein, including any of the pharmaceutical compositions, antibiofilm products, or bandages described herein. Exemplary surfaces suitable for application of the antibiofilm product include, without limitation, a medical device surface, a medical instrument surface, a medical implant surface, a bandage surface, a wound surface, or skin.

The antimicrobial compositions are also effective in preventing a microbial infection or treating the microbial infection in or on a subject. Another aspect of the invention comprises preventing a microbial infection or treating the microbial infection in or on a subject. The method may comprise administering a therapeutically effective amount of any of the compositions described herein or any of the antimicrobial products described herein, including any of the pharmaceutical compositions, antibiofilm products, or bandages described herein. The compositions or antibiofilm products may be administered via oral, intravenous, intramuscular, subcutaneous, topical, and pulmonary route.

Suitably, the microbes described herein may be bacteria, e.g., Gram-negative bacteria or Gram-positive bacteria, whether present in a biofilm or not. In some embodiments, the microbes are drug-resistant bacteria. This includes drug-resistant, Gram-negative bacteria or drug-resistant, Gram-positive bacteria. Exemplary Gram-negative bacteria include, without limitation, *E. coli, A. baumannii, E. cloacae, K. pneumoniae*, and *P. aeruginosa*. Exemplary Gram-positive bacteria include, without limitation, *E. faecium* and *S. aureus*. Exemplary drug-resistant bacteria include, without limitation, carbapenem-resistant bacteria, methicillin-resistant bacteria, or a polymyxin-resistant bacteria. Suitably, biofilms may be formed by or comprise any of the microbes described herein. Suitably, infections may be infections of any of the microbes described herein.

BRIEF DESCRIPTION OF THE DRAWINGS

(FIG. 1A) *Pseudomonas aeruginosa* ATCC 27853; (FIG. 1B) *Staphylococcus aureus* ATCC 29213. Values are expressed as means (number of experiments, 3) and error bars represent standard deviations.

(FIG. 2A) Paenipeptin analogue 17, ceftaroline (Cef), and daptomycin (Dap) against a methicillin-resistant *Staphylococcus aureus* strain LAC. Activity was determined at concentrations corresponding to 5×, 10×, or 20× the concentration corresponding to the MIC for each antibiotic against strain LAC. (FIG. 2B) Analogue 17 and polymyxin B (PMB) against *Pseudomonas aeruginosa* ATCC 27853. Activity was determined at concentrations corresponding to 10×, 20×, 40×, or 80× the concentration corresponding to the MIC for each antibiotic against *P. aeruginosa* ATCC 27853. Results were assessed after 72 h of antibiotic exposure. Values are expressed as means (number of experiments, 6). Means with different letters are significantly different between groups (p<0.05).

(FIG. 3A) *Pseudomonas aeruginosa* ATCC 27853, analogue 17 at 16 µg/mL; (FIG. 3B) *Staphylococcus aureus* ATCC 29213, analogue 17 at 32 µg/mL. Values are expressed as means (number of experiments, at least 3), and error bars represent standard deviations. Means with different letters are significantly different between groups (p<0.05).

(FIG. 4A) *Pseudomonas aeruginosa* ATCC 27853; (FIG. 4B) *Staphylococcus aureus* ATCC 29213. Values are expressed as means (number of experiments, 3) and error bars represent standard deviations. Means with different letters are significantly different between groups (p<0.05).

(FIG. 5A) *Pseudomonas aeruginosa* ATCC 27853; (FIG. 5B) *Staphylococcus aureus* ATCC 29213. Values are expressed as means (number of experiments, 3) and error bars represent standard deviations. Means with different letters are significantly different between groups (p<0.05).

(FIG. 6A) *Acinetobacter baumannii* FDA-CDC AR0063; (FIG. 6B) *Klebsiella pneumoniae* FDA-CDC AR0097. Values are expressed as means (number of independent biological replicates, at least 3) and error bars represent standard deviations. Means at 24 h endpoint with different letters are significantly different between groups (p<0.05).

(FIG. 7A) *Acinetobacter baumannii* FDA-CDC AR0063; (FIG. 7B) *Klebsiella pneumoniae* FDA-CDC AR0097. Values are expressed as means (number of independent biological replicates, at least 3) and error bars represent standard deviations. Means at 24 h endpoint with different letters are significantly different between groups (p<0.05).

DETAILED DESCRIPTION OF THE INVENTION

Figure 1A:
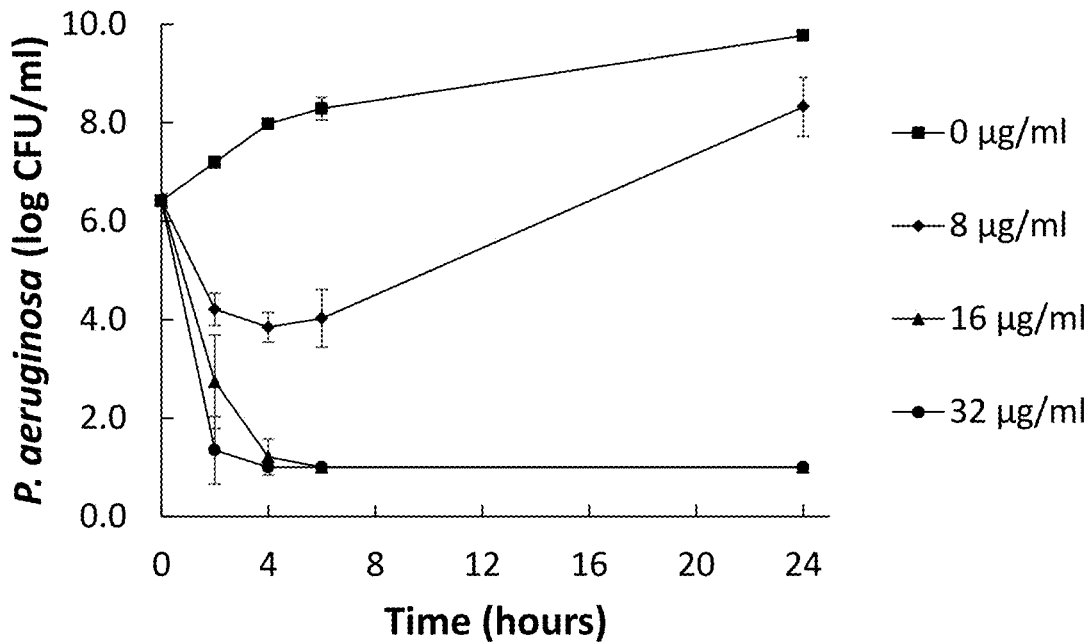
FIGS. 1A-1B show time-kill curves of pathogens with exposure to analogue 17 at 0-32 µg/mL.

Disclosed herein are linear lipopeptide paenipeptins, products comprising the lipopeptides, and methods of using the same. As demonstrated in the Examples that follow, the disclosed lipopeptides have antimicrobial and antibiofilm activity. Without wishing to be bound to theory, it is believed that the paenipeptins disclosed herein disrupt and damage the cytoplasmic membrane of microbes. The disruption of the cytoplasmic membrane can be directly cytotoxic to the microbes, resulting in the paeninpeptin being an antimicrobial agent. In other instances, the disruption of the cytoplasmic membrane can facilitate the transport of other antimicrobial agents to potentiate the cytotoxicity of the other agent. In either instance, the compositions disclosed herein are capable of inhibiting the proliferation of microbes and of treating microbial infections.

The compositions disclosed herein are effective against Gram-negative bacteria, including drug-resistant bacteria. Gram-negative bacteria are intrinsically resistant to large hydrophobic molecules, including many antibiotics, as a result of the permeability barrier of the outer membrane. The integrity of outer the membrane lies in the anionic lipopolysaccharides (LPS) network linked by divalent cations ($Mg^{2+}$ and $Ca^{2+}$) on the cell surface. Cationic lipopeptides such as the paeninpeptins disclosed herein that have affinity for LPS disorganize the outer membrane, providing antimicrobial activity and/or allowing the entry of existing antibiotics. The disclosed lipopeptides have antimicrobial activity and/or sensitize microbes to co-administered antimicrobial agents. As a result, the linear lipopeptides allow for new antimicrobial products and uses thereof.

Linear Lipopeptides

"Linear lipopeptide paenipeptin" (which may also be referred to as "lipopeptide" or "paenipeptin") means a lipopeptide comprising a lipophilic terminus, an amine terminus, and a peptide interposed therebetween. There are three structural features characteristic of the linear lipopeptide paenipeptin: a hydrophobic N-terminal chain, positively-charged residues, and hydrophobic amino acids. As a result, analogues may be readily developed by selecting the length of the lipophilic terminus or the structure of the lipophilic terminus; modulating the cationic character of the lipopeptides; substituting the amino acids, or any combination thereof.

The lipopeptides disclosed herein are compositionally similar to a natural mixture of linear and cyclic lipopeptides produced by *Paenibacillus* sp. OSY-N. [Huang, E. et al. New *Paenibacillus* strain produces a family of linear and cyclic antimicrobial lipopeptides: cyclization is not essential for their antimicrobial activity. *FEMS Microbiology Letters* 2017, 364, herein incorporated by reference in its entirety.] Notably, the use of "linear" in the context of the lipopeptides disclosed herein means that the lipopeptides lack the macrolactone cyclization of the natural cyclic lipopeptides yet retain antimicrobial activity of the paenipeptin family. The development of linear lipopeptide antibiotics is economically beneficial because it significantly simplifies the synthetic process and thus reduces the cost for manufacturing this family of lipopeptides. Most importantly, this allows us access to a large number of linear paenipeptin analogues using standard solid-phase peptide synthesis.

The linear lipopeptide may comprise the formula $R^1$—$X^1$—$X^2$—$X^3$—$X^4$—$X^5$—$X^6$—$X^7$—$X^8$—$X^9$—$NR^2R^3$ where $R^1$ is a lipophilic terminus, $NR^2R^3$ is an amine terminus; and $X^1$—$X^2$—$X^3$—$X^4$—$X^5$—$X^6$—$X^7$—$X^8$—$X^9$ is a nine amino acid peptide interposed therebetween. In some embodiments, the peptide comprises Dab-Ile-Dab-dPhe-Leu-Dab-dVal-Leu-Ser (SEQ ID NO: 1) or a derivative thereof. Derivatives of SEQ ID NO: 1 may comprise at least one substituted amino acid. In particular embodiments, the derivative may comprise one amino acid substitution (i.e., 88% sequence identity to SEQ ID NO: 1), two independently selected amino acid substitutions ((i.e., 77% sequence identity to SEQ ID NO: 1), or three independently selected amino acid substitutions (i.e., 66% sequence identity to SEQ ID NO: 1). In particular embodiments the substituted amino acid is selected from lipophilic amino acids and/or cationic amino acids.

The substituted amino acid may be a proteinogenic amino acid or a nonproteinogenic amino acid. "Proteinogenic amino acids" include any of the L-isomers of lipophilic amino acids [i.e., alanine (Ala), isoleucine (Ile), leucine (Leu), methionine (Met), phenylalanine (Phe), tryptophan (Trp), tyrosin (Tyr), or valine (Val)], cationic amino acids [i.e., arginine (Arg), histidine (His), or lysine (Lys)], polar-uncharged amino acids [i.e., serine (Ser), threonine (Thr), asparagine (Asn), or glutamine (Gln)], anionic amino acids [i.e., aspartic acid (Asp) or glutamic acid (Glu)], cysteine (Cys), glycine (Gly), proline (Pro), selenocysteine (Sec), or pyrrolysine (Pyl).

"Nonproteinogenic amino acids" include any of the D-isomers of a proteinogenic amino acid, an unnatural analogue of a proteinogenic amino acid, a functionalized amino acid, or an amino acid having an elongated side chain. "Unnatural analogues of proteinogenic amino acids" include L- and D-isomers of substituted proteinogenic amino acids, β-amino acids having proteinogenic amino acid side chains, or any combination thereof. Substituted proteinogenic amino acids may have one or more substituents selected from alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, amino, or any combination thereof. A "functionalized amino acid" includes an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; and a cyclic amino acid other than proline. Examples of nonproteinogenic amino acids include 2,4-diaminobutyic acid (Dab), 2,3-diaminoproprionic acid (Dap), ornithine (Orn), 4-phenyl-phenylalanine (Phephe), or octylglycine (Octgly).

Derivatives of SEQ ID NO: 1 include, but are not limited to, any of the sequences of SEQ ID NO: 2 to SEQ ID NO: 17 (Table 1). Derivatives of the sequences of SEQ ID NO: 2 to SEQ ID NO: 17 may also be prepared, comprising at least one substituted amino acid as described above. In particular embodiments, the derivative may comprise one amino acid substitution, two independently selected amino acid substitutions, or three independently selected amino acid substitutions.

In certain embodiments of the invention, $X^1$ through $X^9$ may be independently selected from several different amino acids. $X^1$ may be independently selected from Dab, Orn, Dap, Lys, or Arg. $X^2$ may be independently selected from Ile, Val, Phe, Dap, or Phephe. $X^3$ may be independently selected from Dab, Orn, Dap, Lys, Arg, or Thr. $X^4$ may be independently selected from dLeu, dPhe, or Phephe. $X^5$ may be independently selected from Leu, Phe, or Phephe. $X^6$ may be independently selected from Dab, Dap, Orn, Lys, or Arg. $X^7$ may be independently selected from dVal, dLeu, dPhe or Phephe. $X^8$ may be selected from Leu, Phe, Phephe, Octgly. $X^9$ may be independently selected from Ser or Dab. Peptides may comprise any combination thereof.

The lipophilic terminus may be a substituted or unsubstituted, branched or unbranched hydrophobic alkanoyl moiety extending from a terminus of the peptide. The lipophilic terminus may extend from the N-terminus of the peptide. In some embodiments, the lipophilic terminus is a linear, branched, or cyclic alkanoyl extending from the N-terminus via an imide bound. The lipophilic terminus may be a moiety having at least 2 carbon atoms. In some embodiments, the lipophilic terminus has 2 to about 20 (i.e. a $C_2$-$C_{20}$ alkanoyl), about 2 to about 14 (i.e. a $C_2$-$C_{14}$ alkanoyl), about 6 to about 14 (i.e. a $C_6$-$C_{14}$ alkanoyl), or about 6 to about 10 carbon atoms (i.e. a $C_6$-$C_{10}$ alkanoyl).

The alkanoyl may comprise an alkyl moiety, an alkenyl moiety, an alkynyl moiety, a cycloalkyl moiety, a cycloalkenyl moiety, a phenyl moiety, a biphenyl moiety, an amino moiety, an alkoxy moiety, a halo moiety, or any combination thereof. In certain embodiments, the alkanoyl has a general formula R—C(=O)— where R is a alkyl, alkenyl, cycloalkyl, phenylalkyl, biphenylalkyl, alkylamine, cycloalkylamine, phenylalkylamine, biphenylalkylamine, alkoxy, cycloalkoxy, phenylalkoxy, or biphenphylalkoxy. In certain specific embodiments, the alkanoyl has a general formula R—CH(NH$_2$)—C(=O)— and R is a alkyl, alkenyl, cycloalkyl, phenylalkyl, or biphenylalkyl moiety. Examples of lipophilic termini include, without limitation ethanoyl, butanoyl, hexanoyl, heptanoyl, octanoyl, decanoyl, benzoyl, benzyloxycarbonyl, 3-cyclohexylanlanyl, biophenyl-4-carboxyl, 4-phenyl-phenylalanyl, or 4-bromo-phenyl alanyl.

The amine terminus may be any amino moiety extending from a terminus of the peptide. In some embodiments, the amine terminus extends from the C-terminus of the peptide. The amine terminus may be a primary, secondary, or tertiary amine of general formula —NRR' wherein R and R' are independently selected from hydrogen or $C_1$-$C_6$ alkyl moieties.

The lipopeptides may be prepared as a salt. In some embodiments, the lipopeptide may be prepared as a pharmaceutically acceptable salt.

There are three structural features in the cationic lipopeptide paenipeptin: the hydrophobic N-terminal fatty acyl chain, the positively-charged residues, and the hydrophobic amino acids. Exemplary embodiments of the lipopeptides are provided in Table 1. The structure variations in these analogues include, for example, (i) varying the length of the N-terminal fatty acyl chain (e.g., hexanoyl, heptanoyl, octanoyl and decanoyl groups in analogues 1, 3, 8, and 12, respectively); (ii) replacement of the fatty acyl chain with hydrophobic acyl groups (e.g., benzoyl, benzyloxycarbonyl, and 3-cyclohexylalanyl groups in analogues 14, 15, and 16, respectively); (iii) modification of the positively-charged residues (e.g., analogues 9, 10, 11, and 13); and (iv) changing the hydrophobic amino acids in paenipeptin (e.g., analogues 2, 4, 5, 6, 7, and 17).

TABLE 1

Lipopeptide sequence of paenipeptin analogues (An.)

| An. | Name | | Peptide sequences |
|---|---|---|---|
| 1 | C6-Pat | R = Hexanoyl | Dab-Ile-Dab-dPhe-Leu-Dab-dVal-Leu-Ser (SEQ ID: 1) |

TABLE 1-continued

Lipopeptide sequence of paenipeptin analogues (An.)

| An. | Name | Peptide sequences | | |
|---|---|---|---|---|
| 2 | C7Val2-Pat | R = Heptanoyl | | Dab-Val-Dab-dPhe-Leu-Dab-dVal-Leu-Ser (SEQ ID: 2) |
| 3 | C7-Pat | R = Heptanoyl | | Dab-Ile-Dab-dPhe-Leu-Dab-dVal-Leu-Ser (SEQ ID: 1) |
| 4 | C7Phe-2-Pat | R = Heptanoyl | | Dab-Phe-Dab-dPhe-Leu-Dab-dVal-Leu-Ser (SEQ ID: 3) |
| 5 | C7dLeu7-Pat | R = Heptanoyl | | Dab-Ile-Dab-dPhe-Leu-Dab-dLeu-Leu-Ser (SEQ ID: 4) |
| 6 | C7Phe2dLeu7-Pat | R = Heptanoyl | | Dab-Phe-Dab-dPhe-Leu-Dab-dLeu-Leu-Ser (SEQ ID: 5) |

TABLE 1-continued

Lipopeptide sequence of paenipeptin analogues (An.)

| An. | Name | | Peptide sequences |
|---|---|---|---|
| 7 | C7Phe2dLeu7Phe8-Pat | R = Heptanoyl | Dab-Phe-Dab-dPhe-Leu-Dab-dLeu-Phe-Ser (SEQ ID: 6) |

7

| 8 | C8-Pat | R = Octanoyl | Dab-Ile-Dab-dPhe-Leu-Dab-dVal-Leu-Ser (SEQ ID: 1) |

8

| 9 | Dab9-Pat | R = Octanoyl | Dab-Ile-Dab-dPhe-Leu-Dab-dVal-Leu-Dab (SEQ ID: 7) |

9

| 10 | Dab2,9-Pat | R = Octanoyl | Dab-Dab-Dab-dPhe-Leu-Dab-dVal-Leu-Dab (SEQ ID: 8) |

10

| 11 | Orn-Pat | R = Octanoyl | Orn-Ile-Orn-dPhe-Leu-Orn-dVal-Leu-Ser (SEQ ID: 9) |

11

TABLE 1-continued

| Lipopeptide sequence of paenipeptin analogues (An.) | | | |
|---|---|---|---|
| An. | Name | | Peptide sequences |
| 12 | C10-Pat | R = Decanoyl | Dab-Ile-Dab-dPhe-Leu-Dab-dVal-Leu-Ser (SEQ ID: 1) |

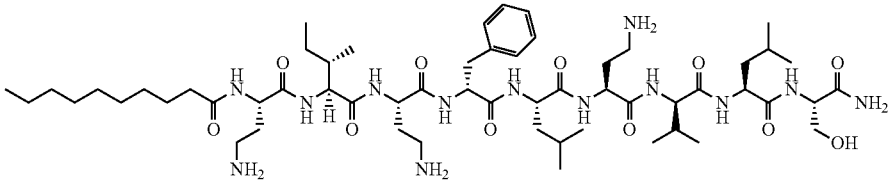

12

| 13 | C10Thr3Leu4-Pat | R = Decanoyl | Dab-Ile-Thr-dLeu-Leu-Dab-dVal-Leu-Ser (SEQ ID: 10) |

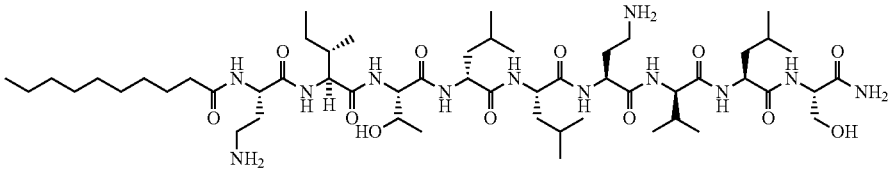

13

| 14 | Benzoyl-Pat | R = Benzoyl | Dab-Ile-Dab-dPhe-Leu-Dab-dVal-Leu-Ser (SEQ ID: 1) |

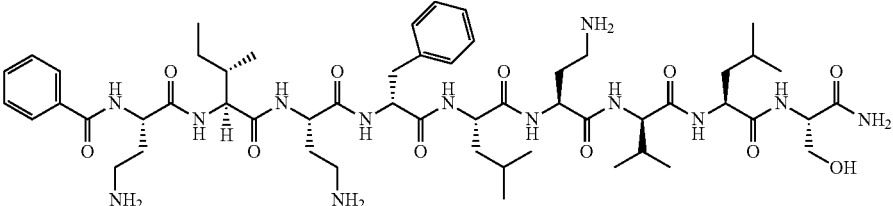

14

| 15 | Cbz-Pat | R = Benzyloxycarbonyl | Dab-Ile-Dab-dPhe-Leu-Dab-dVal-Leu-Ser (SEQ ID: 1) |

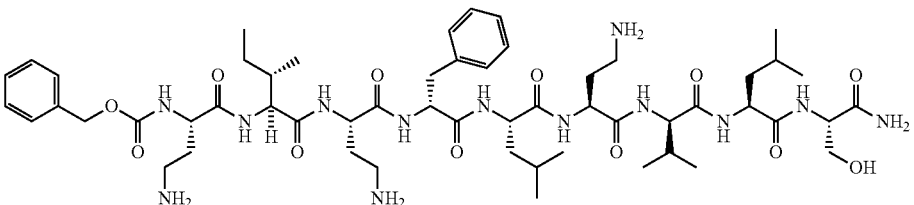

15

| 16 | Cha-Pat | R = 3-cyclohexylalanyl | Dab-Ille-Dab-dPhe-Leu-Dab-dVal-Leu-Ser (SEQ ID: 1) |

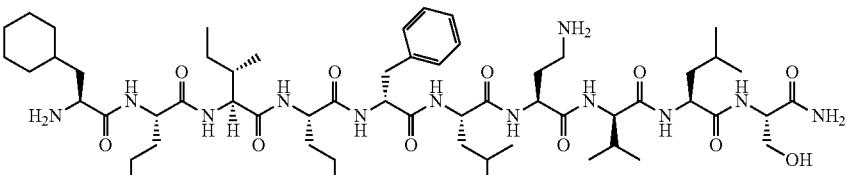

16

TABLE 1-continued

Lipopeptide sequence of paenipeptin analogues (An.)

| An. | Name | | Peptide sequences |
|---|---|---|---|
| 17 | ChaPhe2Leu7Phe8-Pat | R = 3-cyclohexylalanyl | Dab-Phe-Dab-dPhe-Leu-Dab-dLeu-Phe-Ser (SEQ ID: 6) |

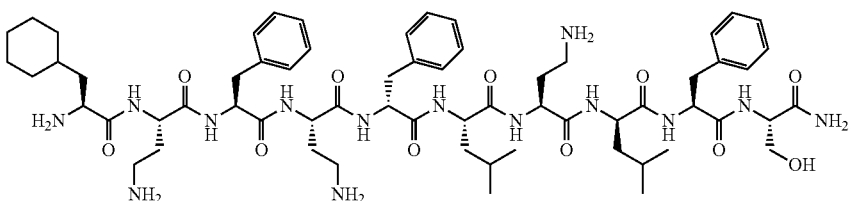

| | | | |
|---|---|---|---|
| 18 | Dap-Pat | R = octanoyl | Dap-Ile-Dap-dPhe-Leu-Dap-dVal-Leu-Ser (SEQ ID: 11) |

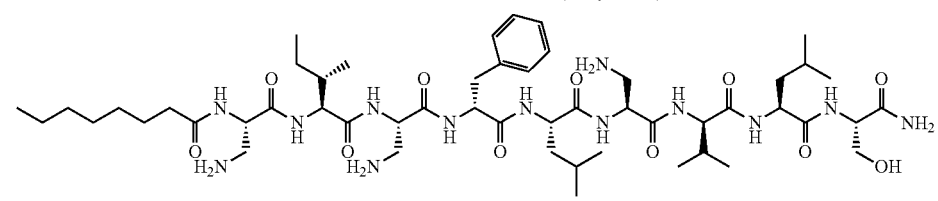

| | | | |
|---|---|---|---|
| 19 | Bip-Pat | R = biphenyl-4-carboxyl | Dab-Ile-Dab-dPhe-Leu-Dab-dVal-Leu-Ser (SEQ ID: 1) |

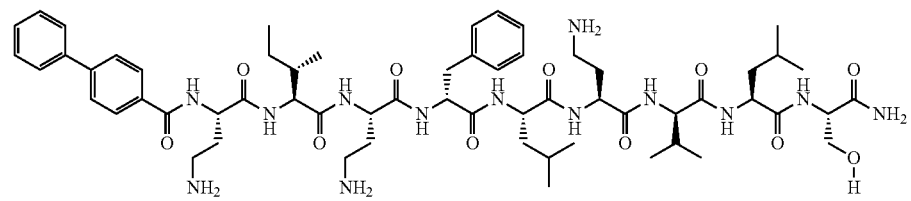 [SMILES: CC[C@H](C)[C@H](NC(=O)[C@H](CCN)NC(=O)c1ccc(-c2ccccc2)cc1)C(=O)N[C@@H](CCN)C(=O)N[C@H](Cc1ccccc1)C(=O)N[C@@H](CC(C)C)C(=O)N[C@@H](CCN)C(=O)N[C@@H](C(=O)N[C@@H](CC(C)C)C(=O)N[C@@H](CO)C(N)=O)C(C)C]

| | | | |
|---|---|---|---|
| 20 | PhePhe-Pat | R = 4-phenyl-phenylalanyl | Dab-Ile-Dab-dPhe-Leu-Dab-dVal-Leu-Ser (SEQ ID: 1) |

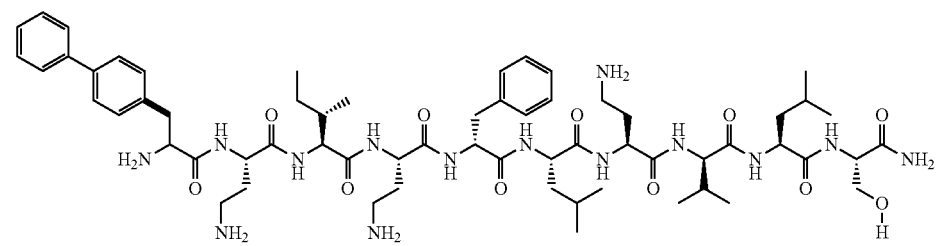

| | | | |
|---|---|---|---|
| 21 | BroPhe-Pat | R = 4-bromo-phenylalanyl | Dab-Ile-Dab-dPhe-Leu-Dab-dVal-Leu-Ser (SEQ ID: 1) |

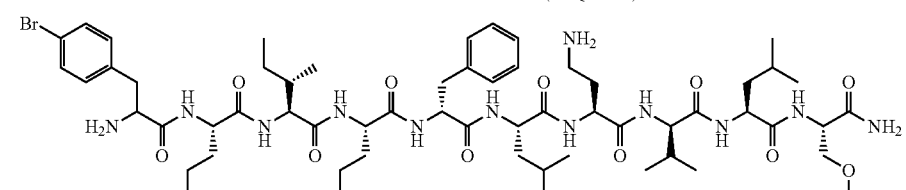

TABLE 1-continued

| An. | Name | | Peptide sequences |
|---|---|---|---|
| 22 | C0-Pat | No R | Dab-Ile-Dab-dPhe-Leu-Dab-dVal-Leu-Ser (SEQ ID: 1) |
| 23 | C2-Pat | R = Acetyl | Dab-Ile-Dab-dPhe-Leu-Dab-dVal-Leu-Ser (SEQ ID: 1) |
| 24 | C4-Pat | R = Butyl | Dab-Ile-dab-dPhe-Leu-Dab-dVal-Leu-Ser (SEQ ID: 1) |
| 25 | ChaPhephe2-Pat | R = 3-cyclohexylalanyl | Dab-Phephe-Dab-dPhe-Leu-Dab-dVal-Leu-Ser (SEQ ID: 12) |
| 26 | ChaPhephe4-Pat | R = 3-cyclohexylalanyl | Dab-Ile-Dab-Phephe-Leu-Dab-dVal-Leu-Ser (SEQ ID: 13) |

TABLE 1-continued

| An. | Name | | Peptide sequences |
|---|---|---|---|
| 27 | ChaPhephe5-Pat | R = 3-cyclohexylalanyl | Dab-Ile-Dab-dPhe-Phephe-Dab-dVal-Leu-Ser (SEQ ID: 14) |
| 28 | ChaPhephe7-Pat | R = 3-cyclohexylalanyl | Dab-Ile-Dab-dPhe-Leu-Dab-Phephe-Leu-Ser (SEQ ID: 15) |
| 29 | Chaphephe8-Pat | R = 3-cyclohexylalanyl | Dab-Ile-Dab-dPhe-Leu-Dab-dVal-Phephe-Ser (SEQ ID: 16) |
| 30 | ChaOctgly8-Pat | R = 3-cyclohexylalanyl | Dab-Ile-Dab-dPhe-Leu-Dab-dVal-Octgly-Ser (SEQ ID: 17) |

[a]Dab: 2,4-diaminobutyric acid;
[b]C8-Pat: lead compound; substituted N-terminal groups and amino acid residues in other analogues are in bold;
[c]Orn: ornithine
[d]Dap: diaminoproprionic acid;
[e]Phephe: 4-phenyl-phenylalanyl;
[f]Octgly: Octylglycyl Antimicrobial Products The compositions disclosed herein expand the antimicrobial spectrum and enhance antibiotic activity of antimicrobial agents such as clarithromycin and rifampicin. As a result lipopeptides themselves or in combination with other antibiotics may be an alternative therapeutic option to treat infections caused by antibiotic-resistant Gram-negative bacteria, including carbapenem-resistant pathogens.

Through the structure-activity relationship studies described herein, potent lipopeptides capable of inhibiting the proliferation of microbes or killing the microbes are identified, including analogues 7, 12 and 17. Analogue 17 showed potent activity against methicillin-resistant *S. aureus* biofilms comparable to that observed with daptomycin and ceftaroline. This new analogue also exhibited strong efficacy against established *P. aeruginosa* biofilms. Therefore, analogue 17 is a promising broad-spectrum antibiotic candidate for targeting drug-resistant pathogens under both planktonic and biofilm-associated conditions. Analogue 9, was non-hemolytic and retained potent *P. aeruginosa*-specific antimicrobial activity. This demonstrates that the lipopeptides disclosed herein may be used as broad-spectrum antimicrobial products or narrow-spectrum antimicrobial products capable of lowering the antibiotic pressure on commensal bacteria.

Many potent large hydrophobic antibiotics, including rifampicin, clarithromycin and erythromycin, are not active against Gram-negative pathogens because of the outer membrane permeability barrier. LPS in the outer membrane of Gram-negative bacteria is the major permeability barrier that excludes such drugs. Considering the urgent need for treating infections caused by multi-drug resistant Gram-negative pathogens, outer membrane permeabilizers, which promote the entry of existing antibiotics, provide an alternative approach to combat antibiotic resistance.

Among the paenipeptin lipopeptides disclosed herein, 10 compounds, which showed little hemolytic activity and were devoid of activity against *A. baumannii* and *K. pneumoniae*, were tested in combination with rifampicin against these two pathogens. When tested at 4 µg/ml, six paenipeptin analogues (1, 3, 9, 14, 15 and 16) decreased the MIC of rifampicin against *A. baumannii* and *K. pneumoniae* from 16 µg/mL (19.42 µM) to nanomolar and subnanomolar levels (sensitization factor: 2,048-8,192). A similar level of synergy was also observed between analogues 9 and 16 and the protein synthesis inhibitor clarithromycin. Therefore, paenipeptins can potentiate different classes of antibiotics that have different modes of action.

Antimicrobial compositions and products may be prepared from the lipopeptides described above. As will be illustrated more fully below, the lipopeptides have antimicrobial activity, antibiofilm activity, and sensitize microbes to other antimicrobial compositions. This allows for the development of several different antimicrobial products, including pharmaceutical compositions or formulations for application to surfaces susceptible to biofilm formation. The compositions may comprise the lipopeptides as the sole antimicrobial agent or the lipopeptides in addition to another antimicrobial agent. Pharmaceutical compositions may also be prepared where the linear peptide may be the sole active pharmaceutical ingredient (API) or used in combination with one or more additional APIs. For formulations for application to surfaces susceptible to biofilm formation, the linear peptide may be the solitary composition having antimicrobial and/or antibiofilm activity or be used in combination with one or more additional compositions having antimicrobial and/or antibiofilm activity.

A lipopeptide having antimicrobial activity means that the lipopeptide is capable of inhibiting the proliferation of a microbe and/or capable of killing a microbe. Suitably, the lipopeptide has a minimum inhibitory concentration less than or equal to 8.0 µg/mL against a microbe in a culture medium and/or a minimum bactericidal concentration less than or equal to 16.0 µg/mL against a microbe in a culture medium. The "minimum inhibitory concentration" (or "MIC") means the lowest concentration of lipopeptide that results in no visible growth of microbial cells after incubation. The "minimum bactericidal concentration" (or "MBC") means the lowest concentration of lipopeptide that leads to at least a 99.9% reduction in the number of viable bacterial cells relative to the initial inoculum. Suitably the lipopeptides may possess either one or both of these properties and be considered to possess antimicrobial activity. Lipopeptides having superior antimicrobial activity are disclosed. Suitably the lipopeptides may have a MIC less than or equal to 6.0 µg/mL, 4.0 µg/mL, 2.0 µg/mL, or 1.0 µg/mL and/or a MBC less than or equal to 14.0 µg/mL, 12.0 µg/mL, 10.0 µg/mL, 8.0 µg/mL, 6.0 µg/mL, 4.0 µg/mL, 2.0 µg/mL, or 1.0 µg/mL. The culture medium may be any suitable solid, liquid or semi-solid designed to support the growth of the microbe, including without limitation tryptic soy broth ("TBS") or a bodily fluid such as serum.

The microbe may be any of a number of different microorganisms such as bacteria, archeae, and yeast. The bacteria may be Gram-negative bacteria, e.g., bacteria of the *Acinetobacter*, *Bartonella*, *Bordetella*, *Borrelia*, *Brucella*, *Campylobacter*, *Enterobacter*, *Escherichia*, *Franisella*, *Haemophilus*, *Helicobacter*, *Klebsiella*, *Legionella*, *Leptospira*, *Moraxella*, *Neisseria*, *Proteus*, *Pseudomonas*, *Rickettsia*, *Salmonella*, *Serratia*, *Shigella*, *Treponema*, *Vibrio*, or *Yersinia* genus, Gram-positive bacteria, e.g., bacteria of the *Bacillus*, *Clostridium*, *Corynebacterium*, *Listeria*, *Staphylococcus*, or *Streptococcus* genus, or bacteria that are neither Gram-negative or -positive, e.g., bacteria of the *Chlamydia*, *Chlamydophila*, *Mycobacterium*, or *Mycoplasma* genus.

The microbe may be a drug-resistant microbe. As used herein, "drug-resistant" means that the MIC of an antimicrobial agent is greater than 32.0 µg/mL in a culture medium. Suitably the microbe is a carbapenem-resistant microbe or a polymyxin-resistant microbe.

In some embodiments, the lipopeptide is not hemolytic and/or cytotoxic. As used herein, a lipopeptide is "non-hemolytic" if the hemolysis percentage is less than or equal to 50.0% at a lipopeptide concentration of 128 µg/mL. Suitably, the hemolysis percentage is less than or equal to 45.0%, 40.0%, 35.0%, 30.0%, 25.0%, 20.0%, 15.0%, 10.0%, or 5.0% at a lipopeptide concentration of 128 µg/mL. As used herein, a lipopeptide is "non-cytoxic" if the viability percentage against the HEK 293 human kidney cell line is greater than or equal to 50.0% at a lipopeptide concentration of 105 µg/mL. Suitably, the viability percentage may be greater than or equal to 55.0%, 60.0%, or 65.0% at a lipopeptide concentration of 105 µg/mL.

The lipopeptides may be used in combination with a number of different antimicrobial agents, sensitizing the microbes to the antimicrobial agent. As used herein, "sensitization factor" means ratio of the MIC of the antimicrobial agent in the absence of the lipopeptide to the MIC of the antimicrobial agent in the presence of 4 µg/mL of the lipopeptide against a microbe. The sensitization factor is greater than or equal to 128 (i.e., $2^7$) for the antimicrobial agent against the microbe. Suitably, the sensitization factor is greater than or equal to 256 (i.e., $2^8$), 512 (i.e., $2^9$), 1024 (i.e., $2^{10}$), 2048 (i.e., $2^{11}$), 4096 (i.e., $2^{12}$), or 8192 (i.e., $2^{13}$)

for the antimicrobial agent against the microbe. As a result of the sensitization provided by the lipopeptide, the antimicrobial agent may be effective in reducing the amount of antimicrobial agent needed to inhibit the proliferation of the microbe from greater than 10 µg/mL to less than 1 µg/mL, 0.1 µg/mL, 0.01 µg/mL, or 0.001 µg/mL. In some cases, this allows for antimicrobial agents to be effective against drug-resistant microbes such as carbapenem- or polymyxin-resistant microbes.

The antimicrobial agents used in combination with the lipopeptides may be an antibiotic that inhibits a cellular pathways and/or the structure or function of a cellular membrane, e.g., a cytoplasmic membrane. For example the antimicrobial agent may inhibit protein synthesis, RNA synthesis, DNA synthesis, metabolism, or cell wall synthesis. Examples of antimicrobial agents capable of performing such functions include, but are not limited to, aminoglycosides, tetracyclines, macrolides, oxazolidinones, streptogramins, licosamides, rifampins, quinolones, novobiocin, trimethoprim, sulfamethoxazole, β-lactams, glycopeptides, tunicamycins, bacitracins, polymyxins, or nisin.

A lipopeptide having antibiofilm activity means that the lipopeptide is capable of inhibiting the proliferation of a microbe and/or capable of killing a microbe on a surface. Suitably, the compositions disclosed herein comprise an effective amount of lipopeptide for an antibiofilm activity of at least a 2.0 log reduction in viable microbes or colony forming units on a surface as compared to the untreated surface. Suitably, the lipopeptide may have an effective amount for a 2.5, 3.0, 3.5, 4.0, 4.5 or 5.0 log reduction in viable microbes on the surface.

The lipopeptides having one or more of the properties described herein may be formulated into antimicrobial products, including pharmaceutical compositions, antibiofilm products, or bandages.

Pharmaceutical Compositions

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutically effective amount may be of the lipopeptide by itself or the combination of the lipopeptide and an antimicrobial agent. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 µM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro-Solv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that treats cancer activity may be administered as a single compound or in combination with another compound that treats cancer or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

Antibiofilm Products

The compounds utilized in the methods disclosed herein may be formulated as antibiofilm compositions that include an effective amount of one or more compounds as disclosed herein formulated for application to a surface to treat or prevent a microbial biofilm on a surface formulated for application to a surface. The effective amount may be of the lipopeptide by itself or the combination of the lipopeptide and an antimicrobial agent. The surface may be any surface where it is desirable to prevent or treat biofilms including, but not limited to, medical devices, medical instruments, medical implants, bandages, wounds, or skin. The antibiofilm product may be formulated in any manner suitable for application to a surface. Examples of formulations include without limitation, sprays, ointments, gels, foams, pastes, hydrogels, or hydrocolloids.

In a particular embodiment, the antibiofilm product is a bandage comprising a dressing and effect amount of one or more compounds as disclosed herein to treat or prevent a microbial infection or a microbial biofilm on a wound. The compounds may be formulated in any of the formulations described above, e.g., sprays, ointments, gels, foams, pastes, hydrogels, or hydrocolloids, and applied to the surface of the dressing or impregnated into the dressing. The dressing may be any dressing suitable for application to a wound, including without limitation, natural and synthetic woven fabrics, such as a gauze, sponges, alginates, collagens, films, gel sheets, wound fillers, hydrogels, or hydrocolloids, or combinations thereof.

Methods of Using the Lipopeptides

The lipopeptides and compositions of the present invention may be used in a variety of ways, including for the inhibition of the proliferation of or killing of a microbe, the prevention of the formation of a biofilm on a surface or the inhibition of the proliferation or killing of a microbe in the biofilm, the prevention of the formation of a biofilm on a wound or skin or the inhibition of the proliferation or killing of a microbe in the biofilm, or the prevention of a microbial infection or the treatment of the microbial infection in a subject.

Methods of Treatment

A use of the compositions described herein is for the prevention of a microbial infection or the treatment of the microbial infection in a subject or on a wound or skin. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a microbial infection of any of the microbes described herein.

As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with the lipopeptides or antimicrobial compounds disclosed herein. For example, a "subject in need of treatment" may include a subject having a microbial disease or condition. Suitably, the microbial disease or condition may be a Gram-negative bacterial infection or Gram-positive bacterial infection, including drug-resistant bacterial infections of either Gram-negative bacteria or Gram-positive bacteria. Exemplary Gram-positive bacterial infections include, without limitation, *E. coli, A. baumannii, E. cloacae, K. pneumoniae*, or *P. aeruginosa* infections. Exemplary Gram-negative bacterial infections include, without limitation, *E. faecium* and *S. aureus* infections. Exemplary drug-resistant bacterial infections include, without limitation, carbapenem-resistant bacteria, methicillin-resistant bacteria, or a polymyxin-resistant bacterial infections.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Methods of Inhibiting the Proliferation or Killing of a Microbe

A use of the compositions described herein is for the inhibition of the proliferation or killing of a microbe. As used herein, the term "inhibiting the proliferation of a microbe" means to retard the growth of microbial cells after incubation with the compositions described herein. Suitably, retarding the growth of microbial cells after incubation may be that there is no visible growth of the microbial cells after incubation. As used herein, the term "killing the microbe" means that there is a reduction in the number of viable microbial cells relative to the initial number of viable microbial cells or inoculum. As used herein the term "effective amount" refers to the amount or dose of the compound, which provides the desired effect. The effective amount may be the MIC of the composition to inhibit the proliferation of the microbes or the MBC of the composition to kill the microbe.

In an alternative aspect of the invention, the lipopeptides may be used to prevent the formation of a biofilm on a surface or to inhibit the proliferation or killing of a microbe in the biofilm. The method comprises contacting a surface or a biofilm disposed thereon with an effective amount of compositions described herein. The lipopeptide may be applied as any suitable formulation for application to a surface. Suitably the surface is a wound or skin. The compositions may be applied to a wound or skin by either direct application onto the wound or indirectly via a bandage comprising the lipopeptide on the surface thereof or impregnated within.

EXAMPLES

Synthesis and Characterization of Paenipeptin Analogues

Paenipeptin analogues were synthesized through a commercial custom peptide service (Genscript Inc., Piscataway, N.J.). Solid-phase peptide synthesis was carried out using Fmoc chemistry on rink amide resin. The resin was pre-swollen in DMF for 1 h before usage. The amidation reaction was achieved by the addition of corresponding amino acid, HOBT and DIC followed by being rocked at room temperature for 1 h. Fmoc protecting group was removed by the treatment of 20% piperidine (v/v) in DMF for 1 h. Between deprotection and coupling, the solid phase peptide synthesis vessel was drained under $N_2$ pressure and washed with DMF for 5 times. A small portion of resin was cleaved and analyzed by HPLC to confirm the conversion. Finally, the resin was treated with a mixture of TFA/TIPS/$H_2O$ (18:1:1, v/v/v) and gently shaken for 2 h. The cleavage solution was filtered and concentrated in vacuo. The crude peptides were purified using preparative-scale $C_{18}$-RP-HPLC. Synthetic lipopeptides were purified by HPLC to homogeneity (≥95% purity) and characterized by high resolution mass spectrometry. The mass spectra (MS) were recorded using Agilent 6210 Time-of-Flight (TOF) LC Mass Spectrometer (Agilent Technologies, Santa Clara, Calif.) at University of California at Riverside. $^1H$ NMR spectra of each paenipeptin analogue were recorded in $D_2O$ on an Agilent 400-MR DD2 Spectrometer (400 MHz) using Tetramethylsilane (TMS) as internal standard. Chemical shifts were reported as δ (ppm) and spin-spin coupling constants as J (Hz) values. Purity, HRMS and $^1H$ NMR data were presented in the supplemental materials.

HPLC Method for Purity Determination

Method A: HPLC analysis was performed using an Alltima C18 column (5 microns, 4.6×250 mm) on a reverse phase HPLC (RP-HPLC) system at a flow rate of 1.0 ml/min. Separation was achieved by a gradient elution using mobile phase A: 0.065% trifluoroacetic acid in 100% water (v/v) and mobile phase B: 0.05% trifluoroacetic acid in 100% acetonitrile (v/v). Elution was detected using a UV monitor at a wavelength of 220 nm. Purity of the target lipopeptides was calculated according to the peak area. Method B: HPLC analysis was performed using a Thermo Scientific BetaSil C18 column (3 microns, 4.6×150 mm) on a reverse phase HPLC (RP-HPLC) system at a flow rate of 0.8 ml/min. Separation was achieved by a gradient elution using mobile phase A: 0.1% trifluoroacetic acid in 100% water (v/v) and mobile phase B: 0.1% trifluoroacetic acid in 100% MeOH (v/v). Elution was detected using a UV monitor at a wavelength of 220 nm. Purity of the target lipopeptides was calculated according to the peak area (Table 2).

TABLE 2

HPLC purity of analogues 1-17

| | Method A | | Method B | |
|---|---|---|---|---|
| Analogue | HPLC purity (%) | Retention time (min) | HPLC purity (%) | Retention time (min) |
| 1 | 96 | 16.4 | 97 | 5.7 |
| 2 | 96 | 18.1 | 96 | 5.7 |
| 3 | 96 | 17.4 | 96 | 7.9 |
| 4 | 97 | 20.5 | 97 | 6.3 |
| 5 | 97 | 21.4 | 99 | 11.5 |
| 6 | 96 | 19.6 | 96 | 9.5 |
| 7 | 96 | 21.0 | 96 | 10.9 |
| 8 | 98 | 18.4 | 96 | 4.9 |
| 9 | 97 | 18.2 | 95 | 4.7 |
| 10 | 95 | 18.0 | 96 | 2.1 |
| 11 | 96 | 19.6 | 99 | 5.6 |
| 12 | 99 | 18.2 | 96 | 19.9 |
| 13 | 95 | 13.1 | 99 | 25.9 |
| 14 | 95 | 18.8 | 97 | 3.5 |
| 15 | 95 | 19.7 | 96 | 4.3 |
| 16 | 95 | 19.9 | 95 | 3.5 |
| 17 | 99 | 19.9 | 99 | 5.4 |

Nuclear Magnetic Resonance and Mass Spectrometry Data of Paenepeptin Analogues

C6-Pat (1)

$^1$H NMR (400 MHz, D$_2$O) δ 7.36-7.01 (m, 5H, D-Phe4-ArH), 4.58 (t, J=8.0 Hz, 1H, D-Phe4-Hα), 4.38-4.10 (m, 6H, Dab1-Hα+Dab3-Hα+Dab6-Hα+Leu5-Hα+Leu8-Hα+Ser9-Hα), 4.00-3.93 (m, 2H, Ile2-Hα+D-Val7-Hα), 3.78-3.67 (m, 2H, Ser9-Hβ), 3.08-2.82 (m, 6H, Dab1-Hγ+Dab3-Hγ+Dab6-Hγ), 2.70-2.45 (m, 2H, D-Phe4-Hβ), 2.14 (t, J=7.4 Hz, 2H, Lipid-Hα), 2.11-1.66 (m, 8H, Dab1-Hβ+Dab3-Hβ+Dab6-Hβ+Ile2-Hβ+D-Val7-Hβ), 1.60-0.93 (m, 14H, Leu5-Hβ, Hγ+Leu8-Hβ, Hγ+Lipid-Hβ, Hγ, Hδ+Ile2-Hγ), 0.85-0.58 (m, 27H, Ile2-Hγ, Hδ+Leu5-Hδ+D-Val7-Hγ+Leu8-Hδ+Lipid-CH$_3$) ppm. HRMS-ESI (m/z) calculated for C$_{53}$H$_{94}$N$_{13}$O$_{11}$ (M+H)$^+$: 1088.7197; Found: 1088.7194.

C7Val2-Pat (2)

$^1$H NMR (400 MHz, D$_2$O) δ 7.31-7.08 (m, 5H, D-Phe4-ArH), 4.56 (t, J=8.0 Hz, 1H, D-Phe4-Hα), 4.37-4.06 (m, 6H, Dab1-Hα+Dab3-Hα+Dab6-Hα+Leu5-Hα+Leu8-Hα+Ser9-Hα), 4.02-3.91 (m, 2H, Val2-Hα+D-Val7-Hα), 3.79-3.67 (m, 2H, Ser9-Hβ), 3.08-2.83 (m, 6H, Dab1-Hγ+Dab3-Hγ+Dab6-Hγ), 2.73-2.48 (m, 2H, D-Phe4-Hβ), 2.16 (t, J=7.4 Hz, 2H, Lipid-Hα), 2.12-1.69 (m, 8H, Dab1-Hβ+Dab3-Hβ+Dab6-Hβ+Val2-Hβ+D-Val7-Hβ), 1.65-0.93 (m, 14H, Leu5-Hβ, Hγ+Leu8-Hβ, Hγ+Lipid-Hβ, Hγ, Hδ, Hε), 0.89-0.59 (m, 27H, Val2-Hγ+Leu5-Hδ+D-Val7-Hγ+Leu8-Hδ+Lipid-CH$_3$) ppm. HRMS-ESI (m/z) calculated for C$_{53}$H$_{94}$N$_{13}$O$_{11}$ (M+H)$^+$: 1088.7197; Found: 1088.7186.

C7-Pat (3)

$^1$H NMR (400 MHz, D$_2$O) δ 7.40-7.04 (m, 5H, D-Phe4-ArH), 4.56 (t, J=8.0 Hz, 1H, D-Phe4-Hα), 4.44-4.06 (m, 6H, Dab1-Hα+Dab3-Hα+Dab6-Hα+Leu5-Hα+Leu8-Hα+Ser9-Hα), 4.00-3.93 (m, 2H, Ile2-Hα+D-Val7-Hα), 3.78-3.67 (m, 2H, Ser9-Hβ), 3.12-2.81 (m, 6H, Dab1-Hγ+Dab3-Hγ+Dab6-Hγ), 2.70-2.48 (m, 2H, D-Phe4-Hβ), 2.16 (t, J=7.5 Hz, 2H, Lipid-Hα), 2.11-1.64 (m, 8H, Dab1-Hβ+Dab3-Hβ+Dab6-Hβ+Ile2-Hβ+D-Val7-Hβ), 1.60-0.95 (m, 16H, Leu5-Hβ, Hγ+Leu8-Hβ, Hγ+Lipid-Hβ, Hγ, Hδ, Hε+Ile2-Hγ), 0.88-0.59 (m, 27H, Ile2-Hγ, Hδ+Leu5-Hδ+D-Val7-Hγ+Leu8-Hδ+Lipid-CH$_3$) ppm. HRMS-ESI (m/z) calculated for C$_{54}$H$_{96}$N$_{13}$O$_{11}$ (M+H)$^+$: 102.7353; Found: 1102.7316.

C7Phe2-Pat (4)

$^1$H NMR (400 MHz, D$_2$O) δ 7.38-6.96 (m, 10H, Phe2-ArH+D-Phe4-ArH), 4.58-4.42 (m, 2H, D-Phe4-Hα+Phe2-Hα), 4.31-4.10 (m, 6H, Dab1-Hα+Dab3-Hα+Dab6-Hα+Leu5-Hα+Leu8-Hα+Ser9-Hα), 3.95 (d, J=7.4 Hz, 1H, D-Val7-Hα), 3.79-3.67 (m, 2H, Ser9-Hβ), 3.08-2.71 (m, 8H, Dab1-Hγ+Dab3-Hγ+Dab6-Hγ+Phe2-Hβ), 2.67-2.47 (m, 2H, D-Phe4-Hβ), 2.10 (t, J=7.5 Hz, 2H, Lipid-Hα), 2.06-1.65 (m, 7H, Dab1-Hβ+Dab3-Hβ+Dab6-Hβ+D-Val7-Hβ), 1.60-0.98 (m, 14H, Leu5-Hβ, Hγ+Leu8-Hβ, Hγ+Lipid-Hβ, Hγ, Hδ, Hε), 0.84-0.60 (m, 21H, Leu5-Hδ+D-Val7-Hγ+Leu8-Hδ+Lipid-CH$_3$) ppm. HRMS-ESI (m/z) calculated for C$_{57}$H$_{94}$N$_{13}$O$_{11}$ (M+H)$^+$: 1136.7197; Found: 1136.7196.

C7dLeu7-Pat (5)

$^1$H NMR (400 MHz, D$_2$O) δ 7.40-7.01 (m, 5H, D-Phe4-ArH), 4.56 (t, J=8.0 Hz, 1H, D-Phe4-Hα), 4.37-4.06 (m, 7H, Dab1-Hα+Dab3-Hα+Dab6-Hα+Leu5-Hα+D-Leu7-Hα+Leu8-Hα+Ser9-Hα), 3.98 (d, J=8.1 Hz, 1H, Ile2-Hα), 3.83-3.66 (m, 2H, Ser9-Hβ), 3.11-2.82 (m, 6H, Dab1-Hγ+Dab3-Hγ+Dab6-Hγ), 2.72-2.47 (m, 2H, D-Phe4-Hβ), 2.16 (t, J=7.4 Hz, 2H, Lipid-Hα), 2.12-1.62 (m, 7H, Dab1-Hβ+Dab3-Hβ+Dab6-Hβ+Ile2-Hβ), 1.62-0.94 (m, 19H, Leu5-Hβ, Hγ+D-Leu7-Hβ, Hγ+Leu8-Hβ, Hγ+Lipid-Hβ, Hγ, Hδ, Hε+Ile2-Hγ), 0.85-0.60 (m, 27H, Ile2-Hγ, Hδ+Leu5-Hδ+D-Leu7-Hδ+Leu8-Hδ+Lipid-CH$_3$) ppm. HRMS-ESI (m/z) calculated for C$_{55}$H$_{98}$N$_{13}$O$_{11}$ (M+H)$^+$: 1116.7510; Found: 1116.7510.

C7Phe2dLeu7-Pat (6)

$^1$H NMR (400 MHz, D$_2$O) δ 7.33-6.99 (m, 10H, Phe2-ArH+D-Phe4-ArH), 4.57-4.42 (m, 2H, Phe2-Hα+D-Phe4-Hα), 4.31-4.10 (m, 7H, Dab1-Hα+Dab3-Hα+Dab6-Hα+Leu5-Hα+D-Leu7-Hα+Leu8-Hα+Ser9-Hα), 3.83-3.66 (m, 2H, Ser9-Hβ), 3.06-2.71 (m, 8H, Dab1-Hγ+Dab3-Hγ+Dab6-Hγ+Phe2-Hβ), 2.68-2.44 (m, 2H, D-Phe4-Hβ), 2.10 (t, J=7.4 Hz, 2H, Lipid-Hα), 2.06-1.65 (m, 6H, Dab1-Hβ+Dab3-Hβ+Dab6-Hβ), 1.62-0.98 (m, 17H, Leu5-Hβ, Hγ+D-Leu7-Hβ, Hγ+Leu8-Hβ, Hγ+Lipid-Hβ, Hγ, Hδ, Hε), 0.84-0.60 (m, 21H, Leu5-Hδ+D-Leu7-Hδ+Leu8-Hδ+Lipid-CH$_3$) ppm. HRMS-ESI (m/z) calculated for C$_{58}$H$_{96}$N$_{13}$O$_{11}$ (M+H)$^+$: 1150.7353; Found: 1150.7335.

C7Phe2dLeu7Phe8-Pat (7)

$^1$H NMR (400 MHz, D$_2$O) δ 7.39-6.96 (m, 15H, Phe2-ArH+D-Phe4-ArH+Phe8-ArH), 4.61-4.41 (m, 3H, Phe2-Hα+D-Phe4-Hα+Phe8-Hα), 4.31-3.98 (m, 6H, Dab1-Hα+Dab3-Hα+Dab6-Hα+Leu5-Hα+D-Leu7-Hα+Ser9-Hα), 3.83-3.66 (m, 2H, Ser9-Hβ), 3.20-2.73 (m, 10H, Dab1-Hγ+Dab3-Hγ+Dab6-Hγ+Phe2-Hβ+Phe8-Hβ), 2.68-2.42 (m, 2H, D-Phe4-Hβ), 2.09 (t, J=7.4 Hz, 2H, Lipid-Hα), 2.04-1.63 (m, 6H, Dab1-Hβ+Dab3-Hβ+Dab6-Hβ), 1.45-0.96 (m, 14H, Leu5-Hβ, Hγ+D-Leu7-Hβ, Hγ+Lipid-Hβ, Hγ, Hδ, Hε), 0.79-0.53 (m, 15H, Leu5-Hδ+D-Leu7-Hδ+Lipid-CH$_3$) ppm. HRMS-ESI (m/z) calculated for C$_{61}$H$_{94}$N$_{13}$O$_{11}$ (M+H)$^+$: 1184.7197; Found: 1184.7200.

C8-Pat (8)

$^1$H NMR (400 MHz, D$_2$O) δ 7.37-6.98 (m, 5H, D-Phe4-ArH), 4.54 (t, J=8.0 Hz, 1H, D-Phe4-Hα), 4.38-4.08 (m, 6H, Dab1-Hα+Dab3-Hα+Dab6-Hα+Leu5-Hα+Leu8-Hα+Ser9-Hα), 4.00-3.93 (m, 2H, Ile2-Hα+D-Val7-Hα), 3.78-3.67 (m, 2H, Ser9-Hβ), 3.10-2.80 (m, 6H, Dab1-Hγ+Dab3-Hγ+Dab6-Hγ), 2.70-2.45 (m, 2H, D-Phe4-Hβ), 2.14 (t, J=7.4 Hz, 2H, Lipid-Hα), 2.10-1.64 (m, 8H, Dab1-Hβ+Dab3-Hβ+Dab6-Hβ+Ile2-Hβ+D-Val7-Hβ), 1.56-0.95 (m, 18H, Leu5-Hβ, Hγ+Leu8-HP, Hγ+Lipid-Hβ, Hγ, Hδ, Hε, Hζ+Ile2-Hγ), 0.85-0.58 (m, 27H, Ile2-Hγ, Hδ+Leu5-Hδ+D-Val7-Hγ+Leu8-Hδ+Lipid-CH$_3$) ppm. HRMS-ESI (m/z) calculated for C$_{55}$H$_{98}$N$_{13}$O$_{11}$ (M+H)$^+$: 1116.7510; Found: 1116.7518.

Dab9-Pat (9)

$^1$H NMR (400 MHz, D$_2$O) δ 7.39-7.02 (m, 5H, D-Phe4-ArH), 4.57 (t, J=8.0 Hz, 1H, D-Phe4-Hα), 4.37-4.11 (m, 6H, Dab1-Hα+Dab3-Hα+Dab6-Hα+Leu5-Hα+Leu8-Hα+Dab9-Hα), 4.02-3.96 (m, 2H, Ile2-Hα+D-Val7-Hα), 3.08-2.84 (m, 8H, Dab1-Hγ+Dab3-Hγ+Dab6-Hγ+Dab9-Hγ), 2.73-2.46 (m, 2H, D-Phe4-Hβ), 2.16 (t, J=7.3 Hz, 2H, Lipid-Hα), 2.12-1.64 (m, 10H, Dab1-Hβ+Dab3-Hβ+Dab6-Hβ+Dab9-Hβ+Ile2-Hβ+D-Val7-Hβ), 1.63-1.00 (m, 18H, Leu5-Hβ, Hγ+Leu8-Hβ, Hγ+Lipid-Hβ, Hγ, Hδ, Hε, Hζ+Ile2-Hγ), 0.83-0.62 (m, 27H, Ile2-Hγ, Hδ+Leu5-Hδ+D-Val7-Hγ+Leu8-Hδ+Lipid-CH$_3$) ppm. HRMS-ESI (m/z) calculated for C$_{56}$H$_{101}$N$_{14}$O$_{10}$ (M+H)$^+$: 1129.7826; Found: 1129.7823.

Dab2,9-Pat (10)

$^1$H NMR (400 MHz, D$_2$O) δ 7.39-7.07 (m, 5H, D-Phe4-ArH), 4.59 (t, J=8.0 Hz, 1H, D-Phe4-Hα), 4.39-4.05 (m, 7H, Dab1-Hα+Dab2-Hα+Dab3-Hα+Dab6-Hα+Leu5-Hα+Leu8-Hα+Dab9-Hα), 4.00 (d, J=7.1 Hz, 1H, D-Val7-Hα), 3.08-2.83 (m, 10H, Dab 1-Hγ+Dab2-Hγ+Dab3-Hγ+Dab6-Hγ+Dab9-Hγ), 2.72-2.52 (m, 2H, D-Phe4-Hβ), 2.17 (t, J=7.3 Hz, 2H, Lipid-Hα), 2.13-1.67 (m, 11H, Dab1-Hβ+Dab2-Hβ+Dab3-Hβ+Dab6-Hβ+Dab9-Hβ+D-Val7-Hβ), 1.60-0.95 (m, 16H, Leu5-Hβ+Leu8-Hβ, Hγ+Lipid-Hβ, Hγ, Hδ, Hε, Hζ), 0.89-0.57 (m, 21H, Leu5-Hδ+D-Val7-Hγ+

Leu8-Hδ+Lipid-CH$_3$) ppm. HRMS-ESI (m/z) calculated for C$_{54}$H$_{98}$N$_{15}$O$_{10}$ (M+H)$^+$: 1116.7622; Found: 1116.7660.

Orn-Pat (11)

$^1$H NMR (400 MHz, D$_2$O) δ 7.31-7.03 (m, 5H, D-Phe4-ArH), 4.56-4.48 (m, 1H, D-Phe4-Hα), 4.39-4.07 (m, 6H, Orn1-Hα+Orn3-Hα+Orn6-Hα+Leu5-Hα+Leu8-Hα+Ser9-Hα), 4.03-3.94 (m, 2H, Ile2-Hα+D-Val7-Hα), 3.83-3.68 (m, 2H, Ser9-Hβ), 3.15-2.80 (m, 6H, Orn1-Hδ+Orn3-Hδ+Orn6-Hδ), 2.80-2.64 (m, 2H, D-Phe4-Hβ), 2.15 (t, J=7.4 Hz, 2H, Lipid-Hα), 2.01-0.92 (m, 32H, Orn1-Hβ, Hγ+Orn3-Hβ, Hγ+Orn6-Hβ, Hγ+Ile2-Hβ, Hγ+D-Val7-Hβ+Leu5-Hβ, Hγ+Leu8-Hβ, Hγ+Lipid-Hβ, Hγ, Hδ, Hε, Hζ, 0.93-0.58 (m, 27H, Ile2-Hγ, Hδ+Leu5-Hδ+D-Val7-Hγ+Leu8-Hδ+Lipid-CH$_3$) ppm. HRMS-ESI (m/z) calculated for C$_{58}$H$_{104}$N$_{13}$O$_{11}$ (M+H)$^+$: 1158.7979; Found: 1158.7989.

C10-Pat (12)

$^1$H NMR (400 MHz, D$_2$O) δ 7.36-7.04 (m, 5H, D-Phe4-ArH), 4.56 (t, J=7.8 Hz, 1H, D-Phe4-Hα), 4.38-4.10 (m, 6H, Dab1-Hα+Dab3-Hα+Dab6-Hα+Leu5-Hα+Leu8-Hα+Ser9-Hα), 4.02-3.95 (m, 2H, Ile2-Hα+D-Val7-Hα), 3.82-3.68 (m, 2H, Ser9-Hβ), 3.10-2.81 (m, 6H, Dab1-Hγ+Dab3-Hγ+Dab6-Hγ), 2.73-2.47 (m, 2H, D-Phe4-Hβ), 2.16 (t, J=7.3 Hz, 2H, Lipid-Hα), 2.12-1.64 (m, 8H, Dab1-Hβ+Dab3-Hβ+Dab6-Hβ+Ile2-Hβ+D-Val7-Hβ), 1.62-0.95 (m, 22H, Leu5-Hβ, Hγ+Leu8-Hβ, Hγ+Lipid-Hβ, Hγ, Hδ, Hε, Hζ, Hη, Hθ+Ile2-Hγ), 0.87-0.60 (m, 27H, Ile2-Hγ, Hδ+Leu5-Hδ+D-Val7-Hγ+Leu8-Hδ+Lipid-CH$_3$) ppm. HRMS-ESI (m/z) calculated for C$_{57}$H$_{102}$N$_{13}$O$_{11}$ (M+H)$^+$: 1144.7823; Found: 1144.7844.

C10Thr3Leu4-Pat (13)

$^1$H NMR (400 MHz, D$_2$O) δ 4.40-3.95 (m, 10H, Dab1-Hα+Ile2-Hα+Thr3-Hα+D-Leu4-Hα+Leu5-Hα+Dab6-Hα+D-Val7-Hα+Leu8-Hα+Ser9-Hα+Thr3-Hβ), 3.80-3.64 (m, 2H, Ser9-Hβ), 3.02-2.84 (m, 4H, Dab1-Hγ+Dab6-Hγ), 2.16 (t, J=7.3 Hz, 2H, Lipid-Hα), 2.11-1.71 (m, 6H, Dab1-Hβ+Dab6-Hβ+Ile2-Hβ+D-Val7-Hβ), 1.62-0.98 (m, 28H, D-Leu4-Hβ, Hγ+Leu5-Hβ, Hγ+Leu8-Hβ, Hγ+Lipid-Hβ, Hγ, Hδ, Hε, Hζ, Hη, Hθ+Ile2-Hγ+Thr3-Hγ), 0.89-0.67 (m, 33H, Ile2-Hγ, Hδ+D-Leu4-Hδ+Leu5-Hδ+D-Val7-Hγ+Leu8-Hδ+Lipid-CH$_3$) ppm. HRMS-ESI (m/z) calculated for C$_{54}$H$_{103}$N$_{12}$O$_{12}$ (M+H)$^+$: 1111.7819; Found: 1111.7803.

Benzoyl-Pat (14)

$^1$H NMR (400 MHz, D$_2$O) δ 7.73-7.34 (m, 5H, Benzoyl-ArH), 7.32-7.05 (m, 5H, D-Phe4-ArH), 4.58-4.46 (m, 2H, D-Phe4-Hα+Dab1-Hα), 4.35-4.06 (m, 5H, Dab3-Hα+Dab6-Hα+Leu5-Hα+Leu8-Hα+Ser9-Hα), 4.02-3.95 (m, 2H, Ile2-Hα+D-Val7-Hα), 3.80-3.65 (m, 2H, Ser9-Hβ), 3.12-2.80 (m, 6H, Dab1-Hγ+Dab3-Hγ+Dab6-Hγ), 2.78-2.49 (m, 2H, D-Phe4-Hβ), 2.25-1.63 (m, 8H, Dab1-Hβ+Dab3-Hβ+Dab6-Hβ+Ile2-Hβ+D-Val7-Hβ), 1.62-0.93 (m, 8H, Leu5-Hβ, Hγ+Leu8-Hβ, Hγ+Ile2-Hγ), 0.91-0.59 (m, 24H, Ile2-Hγ, Hδ+Leu5-Hδ+D-Val7-Hγ+Leu8-Hδ) ppm. HRMS-ESI (m/z) calculated for C$_{54}$H$_{88}$N$_{13}$O$_{11}$ (M+H)$^+$: 1094.6727; Found: 1094.6746.

Cbz-Pat (15)

$^1$H NMR (400 MHz, D$_2$O) δ 7.43-7.02 (m, 10H, D-Phe4-ArH+Cbz-ArH), 5.00 (s, 2H, Cbz-CH$_2$), 4.54 (t, J=7.9 Hz, 1H, D-Phe4-Hα), 4.39-3.98 (m, 8H, Dab1-Hα+Dab3-Hα+Dab6-Hα+Leu5-Hα+Leu8-Hα+Ser9-Hα+Ile2-Hα+D-Val7-Hα), 3.80-3.65 (m, 2H, Ser9-Hβ), 3.11-2.81 (m, 6H, Dab1-Hγ+Dab3-Hγ+Dab6-Hγ), 2.76-2.47 (m, 2H, D-Phe4-Hβ), 2.15-1.68 (m, 8H, Dab1-Hβ+Dab3-Hβ+Dab6-Hβ+Ile2-Hβ+D-Val7-Hβ), 1.61-0.97 (m, 8H, Leu5-Hβ, Hγ+Leu8-Hβ, Hγ+Ile2-Hγ), 0.83-0.56 (m, 24H, Ile2-Hγ, Hδ+Leu5-Hδ+D-Val7-Hγ+Leu8-Hδ) ppm. HRMS-ESI (m/z) calculated for C$_{55}$H$_{90}$N$_{13}$O$_{12}$ (M+H)$^+$: 1124.6833; Found: 1124.6811.

Cha-Pat (16)

$^1$H NMR (400 MHz, D$_2$O) δ 7.37-7.07 (m, 5H, D-Phe4-ArH), 4.60-4.55 (m, 1H, D-Phe4-Hα), 4.50-4.07 (m, 6H, Dab1-Hα, Dab3-Hα+Dab6-Hα+Leu5-Hα+Leu8-Hα+Ser9-Hα), 4.03-3.92 (m, 3H, Ile2-Hα+D-Val7-Hα+Cha-Hα), 3.77-3.70 (m, 2H, Ser9-Hβ), 3.20-2.78 (m, 6H, Dab1-Hγ+Dab3-Hγ+Dab6-Hγ), 2.73-2.39 (m, 2H, D-Phe4-Hβ), 2.23-1.64 (m, 8H, Dab1-Hβ+Dab3-Hβ+Dab6-Hβ+Ile2-Hβ+D-Val7-Hβ), 1.59-0.94 (m, 21H, Leu5-Hβ, Hγ+Leu8-Hβ, Hγ+Ile2-Hγ, Cha-Hβ, Hγ, Hδ, Hε, Hζ), 0.90-0.53 (m, 24H, Ile2-Hγ, Hδ+Leu5-Hδ+D-Val7-Hγ+Leu8-Hδ) ppm. HRMS-ESI (m/z) calculated for C$_{56}$H$_{99}$N$_{14}$O$_{11}$ (M+H)$^+$: 1143.7619; Found: 1143.7636.

ChaPhe2Leu7Phe8-Pat (17)

$^1$H NMR (400 MHz, D$_2$O) δ 7.35-6.95 (m, 15H, Phe2-ArH+D-Phe4-ArH+Phe8-ArH), 4.62-4.00 (m, 9H, Phe2-Hα+D-Phe4-Hα+Phe8-Hα+Dab1-Hα+Dab3-Hα+Dab6-Hα+Leu5-Hα+D-Leu7-Hα+Ser9-Hα), 3.89-3.81 (m, 1H, Cha-Hα), 3.79-3.65 (m, 2H, Ser9-Hβ), 3.19-2.72 (m, 10H, Dab1-Hγ+Dab3-Hγ+Dab6-Hγ+Phe2-Hβ+Phe8-Hβ), 2.65-2.40 (m, 2H, D-Phe4-Hβ), 2.10-1.61 (m, 6H, Dab1-Hβ+Dab3-Hβ+Dab6-Hβ), 1.60-0.73 (m, 19H, Leu5-Hβ, Hγ+D-Leu7-Hβ, Hγ+Cha-Hβ, Hγ, Hδ, Hε, Hζ), 0.70-0.55 (m, 12H, Leu5-Hδ+D-Leu7-Hδ) ppm. HRMS-ESI (m/z) calculated for C$_{63}$H$_{97}$N$_{14}$O$_{11}$ (M+H)$^+$: 1225.7462; Found: 1225.7471.

Antimicrobial Susceptibility Tests

Minimum Inhibitory Concentration (MIC)

The minimum inhibitory concentration (MIC) of paenipeptin analogues was determined using the broth microdilution method (Wirker, M. A. Methods for Dilution Antimicrobial Susceptibility Tests for Bacteria that Grow Aerobically: Approved Standard M07-A8; Clinical and Laboratory Standards Institute, Wayne, Pa., 2009). Seven reference strains (*Acinetobacter baumannii* ATCC 19606, *Escherichia coli* ATCC 25922, *Klebsiella pneumoniae* ATCC 13883, *Pseudomonas aeruginosa* ATCC 27853, *Enterococcus faecium* ATCC 19434, *Staphylococcus aureus* ATCC 29213 and methicillin-resistant *S. aureus* ATCC 43300) were subjected to MIC testing.

Paenipeptin analogues were two-fold diluted in tryptic soy broth (TSB; Becton Dickinson) and mixed with an equal volume of bacterial suspensions in TSB containing approximately 1.5×10$^5$ colony-forming units (CFU)/mL in a clear UV-sterilized 96-well microtiter plate (NBS, Corning Inc., Corning, N.Y.). The total volume was 100 μL and the final paenipeptin concentrations ranged from 0.5-32 μg/mL. The microtiter plate was incubated at 37° C. for 18-20 h. The MIC for each strain was defined as the lowest concentration of each paenipeptin analogue that resulted in no visible growth of bacterial cells after incubation.

The antibacterial activities of these 17 paenipeptin analogues were determined against four Gram-negative and three Gram-positive strains based on determination of the minimum inhibitory concentration (MIC) for each strain. The MIC values of all paenipeptin analogues against the tested bacterial species are listed in Table 3. Antibacterial activity increased with increasing length of the fatty acid chain from C6 to C10 in analogues 1, 3, 8 and 12. Analogues 1 and 3, in which the lipid chains are shorter than C8, were significantly less active than analogue 8. Conversely, analogue 12, which contains a C10 lipid tail, displayed a remarkable increase in antibacterial activity. Replacement of the lipid chain with benzoyl or benzyloxycarbonyl group (analogues 14 and 15) diminished antimicrobial activity, but the 3-cyclohexylalanyl substituent in analogue 16 retained its activity against *E. coli* and *P. aeruginosa* (Table 3).

TABLE 3

Comparison of minimum inhibitory concentration (MIC) of 17 synthetic paenipeptins analogues

| | MIC (µg/ml) | | | | | | |
|---|---|---|---|---|---|---|---|
| An. | A. baumannii ATCC 19606 | E. coli ATCC 25922 | K. pneumoniae ATCC 13883 | P. aeruginosa ATCC 27853 | E. faecium ATCC 19434 | S. aureus ATCC 29213 | S. aureus ATCC 43300 |
| 1 | >32 | 8-16 | ≥32 | 8-16 | >32 | >32 | >32 |
| 2 | >32 | 16 | >32 | 16 | >32 | >32 | >32 |
| 3 | >32 | 4 | 32 | 4 | >32 | >32 | >32 |
| 4 | 32 | 1-4 | 8 | 2-4 | >32 | ≥32 | 32 |
| 5 | 8-16 | 1-4 | 4 | 2-4 | 8-16 | 16-32 | 16 |
| 6 | 8 | 1-4 | 4 | 2-4 | 16 | 16-32 | 16-32 |
| 7 | 2-4 | 0.5-2 | 1 | 1-2 | 8 | 8 | 8 |
| 8 | 16 | 2-4 | 8-16 | 2 | 16 | 8-16 | 8-16 |
| 9 | ≥32 | 4-16 | >32 | 2-4 | 32 | >32 | 32 |
| 10 | >32 | >32 | >32 | 16-32 | >32 | ≥32 | >32 |
| 11 | 32 | 32 | >32 | 16 | >32 | >32 | 32 |
| 12 | 0.5-2 | 2-8 | 2-4 | 1-2 | 2 | 2-4 | 2-4 |
| 13 | >32 | >32 | >32 | >32 | ≥32 | >32 | >32 |
| 14 | >32 | 16-32 | >32 | 8-32 | >32 | >32 | >32 |
| 15 | 16 | 8-16 | >32 | 16 | >32 | >32 | >32 |
| 16 | ≥32 | 4-8 | 32 | 2-8 | >32 | >32 | 32 |
| 17 | 2-4 | 0.5-1 | 2 | 0.5-1 | 8 | 2-4 | 4 |

Compound 8 consists of three positively charged 2,4-diaminobutyric acid (Dab) residues. Replacement of all 3 Dab residues by ornithine (Orn), which possesses an additional carbon on the side chain (analogue 11), unexpectedly abolished antibacterial activity. Alterations of the number of positively-charged residues also had considerable effects on antimicrobial activity. For example, altering the C-terminal Ser to Dab at position 9 (analogue 9) resulted in an increase in MIC for all bacterial species except *P. aeruginosa*. Similarly, adding one additional Dab at position 2 (analogue 10) or reducing the Dab charge at position 3 (analogue 13) resulted in the loss of almost all antibacterial activity. In contrast, changes associated with increased hydrophobicity were associated with increases in antibacterial activity. For example, analogues 3 and 4 have more hydrophobic residues (Ile or Phe) at position 2 were more potent than analogue 2, which has a Val residue at the same position. Replacement of Val by Leu at position 7 (analogue 5) also showed an increase in antimicrobial activity. Further increases in hydrophobicity in analogues 6, 7, and 17 significantly enhanced antibacterial activity against all bacterial strains tested (Table 3).

Minimum Inhibitory Concentration (MIC) for Antibiotic Resistant Strains

In addition to the above reference strains, the susceptibility of nine carbapenem-resistant isolates and six polymyxin-resistant strains (Tables 4 and 5), including clinical isolates from the FDA-CDC Antibiotic Resistance Bank, were tested for the selected paenipeptin analogue 17. There were at least three independent experiments with one replicate in each experiment.

Paenipeptin analogue 17 is the most active compound among 17 rationally-designed analogues. Therefore, this analogue was further evaluated for its in vitro efficacy against drug-resistant Gram-negative bacteria. Paenipeptin analogue 17 showed potent activity with an MIC of 0.5-2 µg/ml against nine carbapenem-resistant clinical isolates from the FDA-CDC Antibiotic Resistance Bank, including *A. baumannii, Enterobacter cloacae, E. coli, K pneumoniae*, and *P. aeruginosa* (Table 4). In addition, analogue 17 was active against polymyxin-resistant *E. coli* and *K. pneumoniae* strains, including a strain carrying the polymyxin resistance gene mcr-1 (Table 5).

TABLE 4

Minimum inhibitory concentration (µg/mL) of analogue 17 against carbapenem-resistant pathogens from the FDA-CDC Antibiotic-Resistance (AR) Bank

| FDA-CDC AR Bank # | Strains | Known resistance [a] | Analogue 17 (µg/ml) |
|---|---|---|---|
| 063 | Acinetobacter baumannii | OXA-23, 24/40 | 0.5 |
| 083 | A. baumannii | OXA-23, NDM | 2 |
| 038 | Enterobacter cloacae | NDM | 0.5 |
| 053 | E. cloacae | KPC-3, TEM-1 | 0.5 |
| 048 | Escherichia coli | NDM | 0.5 |
| 061 | E. coli | KPC-3, TEM-1 | 0.5-1 |
| 068 | Klebsiella pneumoniae | NDM, OXA-181 | 0.5-2 |
| 097 | K pneumoniae | KPC | 1-2 |
| 064 | Pseudomonas aeruginosa | SPM | 2 |

[a] Production of various types of beta-lactamase

TABLE 5

Minimum inhibitory concentration (µg/mL) of analogue 17 against polymyxin-resistant strains

| Strains | Analogue 17 (µg/ml) | Polymyxin B (µg/ml) |
|---|---|---|
| Escherichia coli AR 0494[a] | 0.5 | 2-8 |
| E. coli UAMS-ECPR1[b] | <0.5 | 32 |
| E. coli UAMS-ECPR2[b] | <0.5 | 32 |
| Klebsiella pneumoniae AR 0109[a] | 4-8 | 16-32 |
| K. pneumoniae UAMS-KPPR1[c] | 2 | >32 |
| K. pneumoniae UAMS-KPPR3[c] | 2 | >32 |

[a] Bacterial strains were obtained from the FDA-CDC Antibiotic-Resistance Bank, *Escherichia coli* AR 0494 carries the plasmid-encoded polymyxin resistance gene, mcr-1;
[b] strains are the derivatives of *E. coli* ATCC 25922;
[c] strains are the derivatives of *K. pneumoniae* ATCC 13883

Minimum Bactericidal Concentration (MBC)

Minimum bactericidal concentration (MBC) of paenipeptin analogues was determined at the end point of MIC tests by sub-culturing an aliquot of 50 µL cell suspension from the 96-well microtiter plate used for MIC testing. The surviving cells from each antimicrobial concentration with no visible growth were enumerated by plating on tryptic soy agar (TSA). MBC was defined as the lowest concentration of the antimicrobial agent that led to at least a 99.9% reduction in the number of viable bacterial cells relative to the initial inoculum. There were three independent experiments with one replicate in each experiment.

Six paenipeptin analogues (5, 6, 7, 8, 12, and 17) showing potent and broad antibacterial activity were chosen to determine their minimum bactericidal activity (MBC) against the same four Gram-negative and three Gram-positive strains. Analogues 9 and 16 showed narrow activity against Pseudomonas; therefore the MBC of these analogues was only determined for P. aeruginosa. The MBC values of selected paenipeptin analogues are listed in Table 6. Compared to the lead compound (analogue 8), three new paenipeptin analogues (7, 12, and 17) displayed a 2-8 fold increase in their bactericidal activity against most bacterial strains tested (Table 6).

Ohio). Paenipeptin analogues were two-fold diluted in 100% human serum and mixed with an equal volume of 90% serum containing approximately $1.5 \times 10^5$ CFU/mL of E. coli ATCC 25922 or S. aureus ATCC 29213. The final paenipeptin concentrations ranged from 0.5-64 μg/mL in 95% serum. The MIC in the presence of serum was then tested as described above.

To determine the stability of peptides in human serum, paenipeptin analogues were added into 100% human serum to a final concentration of 64 μg/ml. The mixtures were incubated at 37° C. and samples were withdrawn at 0, 6, 12 and 24 h. The treated paenipeptin analogues were two-fold diluted in 100% human serum and mixed with an equal volume of E. coli ATCC 25922 cells in TSB (approximately $1.5 \times 10^5$ CFU/mL) for MIC determination. The residual

TABLE 6

Comparison of minimum bactericidal concentration (MBC) of 8 selected synthetic paenipeptin analogues

| | MBC (μg/ml) | | | | | | |
|---|---|---|---|---|---|---|---|
| Analogue | A. baumannii ATCC 19606 | E. coli ATCC 25922 | K. pneumoniae ATCC 13883 | P. aeruginosa ATCC 27853 | E. faecium ATCC 19434 | S. aureus ATCC 29213 | S. aureus ATCC 43300 |
| 5 | 16 | 16 | 8 | 8-16 | 16 | 16-32 | 16-32 |
| 6 | 8 | 32 | 8 | 8-16 | 32 | 16-32 | 32 |
| 7 | 4 | 8-16 | 2 | 4 | 16 | 8-32 | 8-16 |
| 8 | 16-32 | 16 | 8-16 | 8-16 | 16-32 | 16 | 8-32 |
| 9 | ND[a] | ND | ND | 16 | ND | ND | ND |
| 12 | 0.5-2 | 8 | 4-8 | 2-4 | 2-4 | 4-8 | 2-4 |
| 16 | ND | ND | ND | 16-32 | ND | ND | ND |
| 17 | 4-8 | 8-16 | 4 | 2-4 | 16 | 8 | 8 |

Figure 1B:
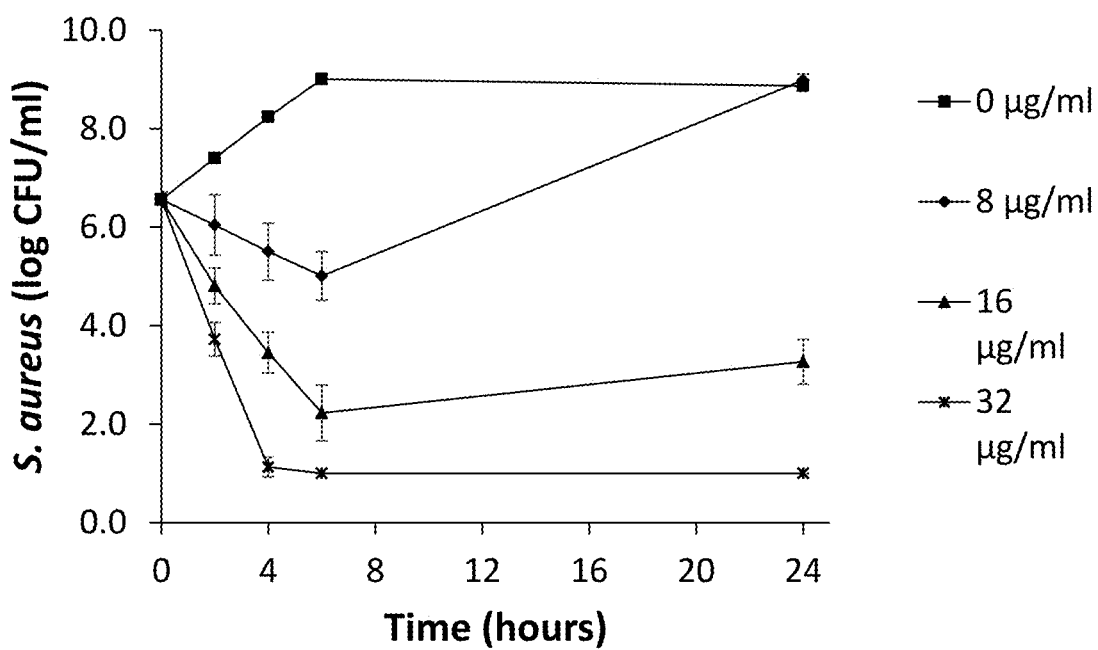

[a]ND: not determined because of relatively high minimum inhibitory concentration Time Kill Assay Time-kill kinetics of analogue 17 were determined at three concentrations (8, 16 and 32 μg/ml) using the reference strains P. aeruginosa ATCC 27853 and S. aureus ATCC 29213. The surviving cells after antimicrobial treatment were enumerated at 0, 2, 4, 6 and 24 h by plating on TSA. There were three independent experiments with one replicate in each experiment Time-kill assays were performed with analogue 17, which was the most effective analogue against both P. aeruginosa ATCC 27853 and S. aureus ATCC 29213. This was done at three different concentrations (8, 16 and 32 μg/ml). Analogue 17 showed a concentration dependent bactericidal effect against both pathogens. For example, the number of viable P. aeruginosa cells was reduced by 5.1 logs and 3.7 logs within 2 h when exposed to analogue 17 at 32 μg/ml and 16 μg/ml, respectively, and no viable cells were detected after 24 h exposure to either concentration. Analogue 17 at 8 μg/ml resulted in a 2.2 log reduction of viable P. aeruginosa cells in 2 h but significant bacterial regrowth was observed at 24 h (FIG. 1A). It took longer for analogue 17 to achieve a similar reduction in the number of viable S. aureus cells. Specifically, exposure to analogue 17 at 32 μg/ml and 16 μg/ml reduced the number of viable S. aureus cells by 5.4 logs and 3.1 logs, respectively, but only after 4 h. Regrowth of S. aureus was also observed when the cells were exposed to analogue 17 at 8 μg/ml (FIG. 1B).

Impact of Human Serum on Antibacterial Activity and Stability

The impact of human serum on the antibacterial activity of selected paenipeptin analogues was determined using a procedure similar to that used for MIC determination as described above except that the microbiological medium was replaced by human serum (MP Biomedicals, Solon, antibacterial activity after incubation in human serum was compared to the non-treated control.

Human serum inhibited the growth of P. aeruginosa ATCC 27853 and K. pneumoniae ATCC 13883 (data not shown); therefore, other reference strains (E. coli ATCC 25922 and S. aureus ATCC 29213) that grew in 95% serum were used to test the antibacterial efficacy of paenipeptin analogues in the presence of human serum. In human serum, analogues 9 and 16 showed potent activity against E. coli, while analogue 9 exhibited a slight increase in activity against S. aureus (Table 7). However, other analogues showed reductions in antimicrobial activity in the presence of human serum. For example, analogue 17 showed 8 to 16-fold increase in MIC against both E. coli and S. aureus, which corresponds to 88-94% reduction in its activity. It is generally believed that human serum proteins can bind to certain lipopeptide antibiotics and limit their antibacterial activity. For example, the MIC of lipopeptide MX-2401 against S. aureus ATCC 29213 increased from 2 μg/ml in microbiological medium to 128 μg/ml in 95% mouse serum; this corresponded to 98.9% protein binding. However, the degree of protein binding cannot be used to accurately predict the ultimate therapeutic performance of antibiotics. For instance, daptomycin is a lipopeptide highly bound to plasma proteins (94%), but it is an effective drug recently approved to treat infections caused by methicillin-resistant S. aureus.

Among eight paenipeptin analogues tested in the presence of 95% human serum, four analogues (8, 9, 16 and 17) showed relatively high activity against E. coli (Table 7), thus these four analogues were further tested for their stability at 37° C. in human serum. Analogue 16 showed an increase in its MIC from 1-2 μg/ml to >32 μg/ml after incubation in serum for 6 h, which indicates that analogue 16 may not be stable at 37° C. in human serum (Table 8). Specifically, analogue 16 displayed a relatively low MIC (2 µg/ml) in human serum against *E. coli* (Table 7) but lost its efficacy after an extended incubation time at 37° C. in serum. This suggests that analogue 16 may rapidly kill bacterial cells but is inactivated by serum components over time. Importantly, the other three analogues tested (8, 9, and 17) showed little decrease in antibacterial activity after incubation in human serum at 37° C. for up to 24 h (Table 8). Analogue 8 differs from analogue 16 in the N-terminal modifications. Based on this, the N-terminal lipid chain in analogue 8 may be associated with its high stability in human serum. However, the hydrophobic group (3-cyclohexylalanyl) in analogue 16 did not protect it from being inactivated in serum. Analogues 16 and 17 shared the same N-terminal modification, but the latter became more stable when three amino acids in positions 2, 7, and 8 were substituted with more hydrophobic residues.

TABLE 7

Impact of human serum on antimicrobial activity of selected paenipeptin analogues

| | Minimum inhibitory concentration (µg/ml) | | | |
|---|---|---|---|---|
| | *Escherichia coli* ATCC 25922 | | *Staphylococcus aureus* ATCC 29213 | |
| Analogue | 95% serum | TSB broth | 95% serum | TSB broth |
| 5 | 16 | 1-4 | 32 | 16-32 |
| 6 | 32 | 1-4 | 64 | 16-32 |
| 7 | 32 | 0.5-2 | 32-64 | 8 |
| 8 | 8 | 2-4 | 16-32 | 8-16 |
| 9 | 2-4 | 4-16 | 16 | >32 |
| 12 | 32 | 2-8 | 16 | 2-4 |
| 16 | 2 | 4-8 | >64 | >32 |
| 17 | 8 | 0.5-1 | 32 | 2-4 |

TABLE 8

Stability of selected paenipeptin analogues in human serum at 37° C.$^a$

| | Minimum inhibitory concentration (µg/ml) | | | |
|---|---|---|---|---|
| Analogue | 0 h | 6 h | 12 h | 24 h |
| 8 | 8 | 8 | 8 | 8 |
| 9 | 1-2 | 2 | 1-2 | 2 |
| 16 | 1-2 | >32 | >32 | >32 |
| 17 | 4-8 | 4-8 | 4-8 | 8 |

$^a$MIC was determined against *Escherichia coli* ATCC 25922

Hemolytic Activity

Hemolytic activity was evaluated using defibrinated rabbit blood in a 96-well plate as described previously. A nonionic surfactant Triton X-100, which is capable of lysing red blood cells (RBCs), was used at 0.1% as a positive control. Briefly, rabbit blood (Hardy Diagnostics, Santa Maria, Calif.) was diluted with phosphate buffered saline (PBS; pH 7.2) at a 1:19 ratio (v/v) and free hemoglobin was removed by washing RBCs and centrifugation four times at 1,000×g at 4° C. for 5 min. Aliquots (50 µL) of washed RBCs were incubated with 150 µL two-fold dilutions of paenipeptin analogues at final concentrations of 16-128 µg/mL at 37° C. for 30 min in a microtiter plate (NBS, Corning Inc.). After incubation, treated RBCs were gently mixed by repeated pipetting. Aliquots (20 µL) of the cell suspension were mixed with 200 µL PBS in a new 96-well plate and centrifuged at 2,204×g for 10 min. The supernatant was transferred to a new 96-well plate for absorbance measurement at 415 nm using a Cell Imaging Multimode Reader (Cytation 3, BioTek; Winooski, Vt.). The percent hemolysis observed after exposure to each paenipeptin analogue was calculated relative to Triton X-100. There were at least three independent experiments with one replicate in each experiment.

Alteration of the N-terminal lipid chain had a substantial impact on paenipeptin hemolytic activity. Among analogues 1, 3, 8, and 12, hemolytic activity against rabbit red blood cells increased as the lipid chain length increased from C6 to C10. Specifically, analogues 1 and 3 with a C6 and C7 lipid chain, respectively, displayed little hemolysis at 128 µg/mL, whereas at the same concentration, analogue 12 carrying a C10 lipid chain showed strong hemolytic activity (Table 9). Importantly, these same trends were reflected in relative antibacterial activity, which also increased with increasing chain length. By contrast, replacing the fatty acid chain with hydrophobic groups in analogues 14, 15, and 16 greatly reduced their hemolytic activity. These results are in agreement with previous reports where replacing the fatty acid chain with aromatic groups reduced the toxicity of lipopeptide polymyxins. However, as noted above, replacing the fatty acid chain with hydrophobic groups in analogues 14 and 15 also resulted in reduced antibacterial activity.

Analogues 9 and 16, which retained their activity against *P. aeruginosa*, were non-hemolytic at 128 µg/mL (Table 9), thus these two paenipeptin derivatives could be further developed as narrow spectrum anti-*Pseudomonas* agents. Among C7 paenipeptin derivatives (analogues 2-7), hemolytic activity increased when more hydrophobic amino acids were introduced into the peptide chain. One exception was analogue 6, which was more hydrophobic but much less hemolytic than analogue 5. By comparison to compound 8, analogue 17 showed at least a 4-fold improvement in antibacterial activity against *A. baumannii* and *K. pneumoniae* (Table 3) but at the expense of a 37% increase in hemolytic activity (Table 9).

TABLE 9

Comparison of hemolytic activity$^a$ of 17 paenipeptin analogues against rabbit red blood cells

| | Hemolysis (%) | | | |
|---|---|---|---|---|
| Analogue | 128 µg/mL | 64 µg/mL | 32 µg/mL | 16 µg/mL |
| 1 | 0.61 ± 0.25 | 0.08 ± 0.85 | 0.41 ± 0.58 | 0.48 ± 0.64 |
| 2 | 0.95 ± 0.45 | 0.79 ± 0.63 | 0.32 ± 0.74 | -0.17 ± 0.19 |
| 3 | 1.77 ± 0.81 | 1.18 ± 0.68 | 0.78 ± 0.30 | 0.18 ± 0.54 |
| 4 | 1.28 ± 1.65 | 0.60 ± 1.35 | 0.49 ± 1.22 | 0.28 ± 1.11 |
| 5 | 26.5 ± 4.45 | 4.86 ± 1.05 | 1.39 ± 0.55 | 0.96 ± 0.59 |
| 6 | 8.34 ± 1.80 | 2.03 ± 0.44 | 0.39 ± 0.30 | 0.14 ± 0.20 |
| 7 | 64.2 ± 3.28 | 18.8 ± 2.44 | 5.10 ± 1.26 | 0.99 ± 0.31 |
| 8 | 25.3 ± 4.15 | 6.18 ± 2.48 | 1.91 ± 0.25 | 0.93 ± 0.45 |
| 9 | 2.25 ± 2.18 | 0.73 ± 0.50 | 0.80 ± 0.68 | 0.52 ± 0.58 |
| 10 | 0.80 ± 0.40 | 0.41 ± 0.53 | 0.38 ± 0.62 | 0.37 ± 0.62 |
| 11 | 1.12 ± 0.47 | 0.69 ± 0.64 | 0.44 ± 0.30 | 0.86 ± 0.72 |
| 12 | 93.9 ± 7.57 | 73.4 ± 7.59 | 37.2 ± 8.62 | 14.3 ± 4.25 |
| 13 | 24.9 ± 2.71 | 10.0 ± 1.03 | 5.06 ± 1.14 | 1.25 ± 0.71 |
| 14 | 0.70 ± 0.34 | 1.14 ± 1.05 | 0.71 ± 0.82 | 0.22 ± 0.17 |
| 15 | 0.65 ± 0.29 | 0.54 ± 0.70 | 0.41 ± 0.67 | 0.77 ± 0.15 |
| 16 | 1.63 ± 0.40 | 0.65 ± 0.62 | 0.33 ± 0.83 | 0.55 ± 0.75 |
| 17 | 34.6 ± 0.91 | 11.02 ± 0.99 | 2.46 ± 0.34 | 0.60 ± 0.18 |

$^a$Percent hemolysis was calculated relative to the positive control, Triton X-100.

Cytotoxicity

Cytotoxicity of paenipeptin analogues was determined against a human kidney cell line (HEK 293) using MTT assays (Huang E, Yousef AE. 2014. Paenibacterin, a novel broad-spectrum lipopeptide antibiotic, neutralises endotoxins and promotes survival in a murine model of *Pseudomonas aeruginosa*-induced sepsis. Int J Antimicrob Agents 44: 74-77). Cell viability was measured at 24 h following the addition of lipopeptides at concentrations between 30-105 µg/ml. The viability of human embryonic kidney cells (HEK 293) decreased with the increase of paenipeptin concentration. The viability of HEK 293 cells in the presence of paenipeptin analogue 1 and 15 at 105 µg/ml was 61% and 67%, respectively (Table 10). The relatively low cytotoxicity of paenipeptin analogue 1 and 15 was correlated with their low hemolytic activity against red blood cells.

TABLE 10

Viability (%) of human embryonic kidney cells (HEK 293) after the treatment of paenipeptin analogues 1 and 15 for 24 h

| An. | 30 µg/ml | 45 µg/ml | 60 µg/ml | 75 µg/ml | 90 µg/ml | 105 µg/ml |
|---|---|---|---|---|---|---|
| 1 | 85.23 ± 10.15 | 78.41 ± 11.15 | 78.43 ± 13.49 | 73.09 ± 11.35 | 69.03 ± 8.14 | 61.01 ± 6.38 |
| 15 | 91.39 ± 4.09 | 84.32 ± 8.12 | 82.04 ± 4.54 | 73.34 ± 5.37 | 67.13 ± 10.03 | 67.47 ± 9.66 |

Antibiofilm Activity

The effect of paenipeptin analogue 17 on established *S. aureus* or *P. aeruginosa* catheter-associated biofilms was determined in vitro as described previously with minor modifications.[18] Briefly, 1-cm segments (n=6) of fluorinated ethylene propylene catheters (14 gauge; Introcan safety catheter; B. Braun, Bethlehem, Pa.), were pre-coated with 20% human plasma overnight before being placed into 2 mL biofilm medium (TSB supplemented with 0.5% glucose and 3.0% NaCl) in the wells of a 24-well microtiter plate (ultra-low attachment surface; Corning Inc.). Each well was inoculated with the methicillin-resistant *S. aureus* strain LAC or *P. aeruginosa* ATCC 27853 to an $OD_{600nm}$ of 0.05. After incubation at 37° C. for 24 h, catheters with established biofilms were transferred to freshly made biofilm medium with or without paenipeptin analogue 17 at concentrations corresponding to 5, 10, and 20× its MIC for the *S. aureus* LAC strain or 10, 20, 40, and 80× its MIC for *P. aeruginosa* ATCC 27853. The MIC values of analogue 17 against LAC and *P. aeruginosa* ATCC 27853 were 8 µg/mL and 1 µg/ml, respectively. Six catheters colonized with each strain and exposed to each concentration were removed at daily intervals and transferred to fresh medium containing the same concentration of analogue 17. After 72 h of exposure, catheters were rinsed with PBS, followed by sonication (for *S. aureus*) or vigorous vortexing (for *P. aeruginosa*) to quantitatively recover adherent bacteria. Viable *S. aureus* or *P. aeruginosa* cells were enumerated by plating serial dilutions on TSA. Ceftaroline and daptomycin at a concentration of 20× the MIC for each antibiotic were used as positive controls in the context of biofilms formed with the *S. aureus* strain LAC. Polymyxin B was used as a positive control at a concentration 20× its MIC (10 µg/ml) as a positive control in the context of biofilms formed by *P. aeruginosa* ATCC 27853.

Figure 2A:
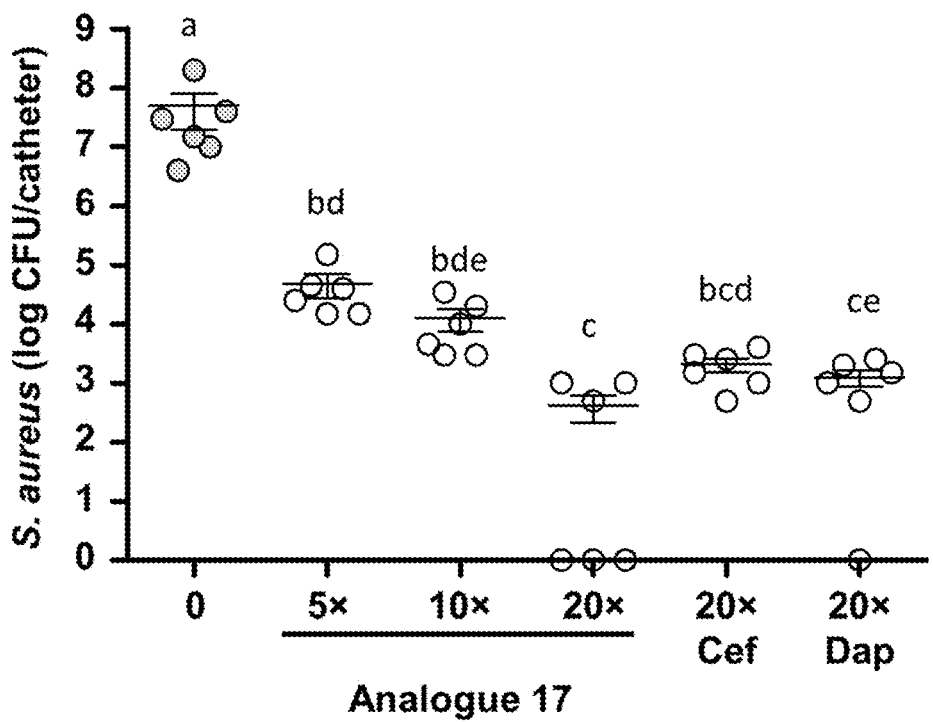
FIGS. 2A-2B show relative activity of antibiotics against established biofilms on catheters in vitro.
Figure 2B:
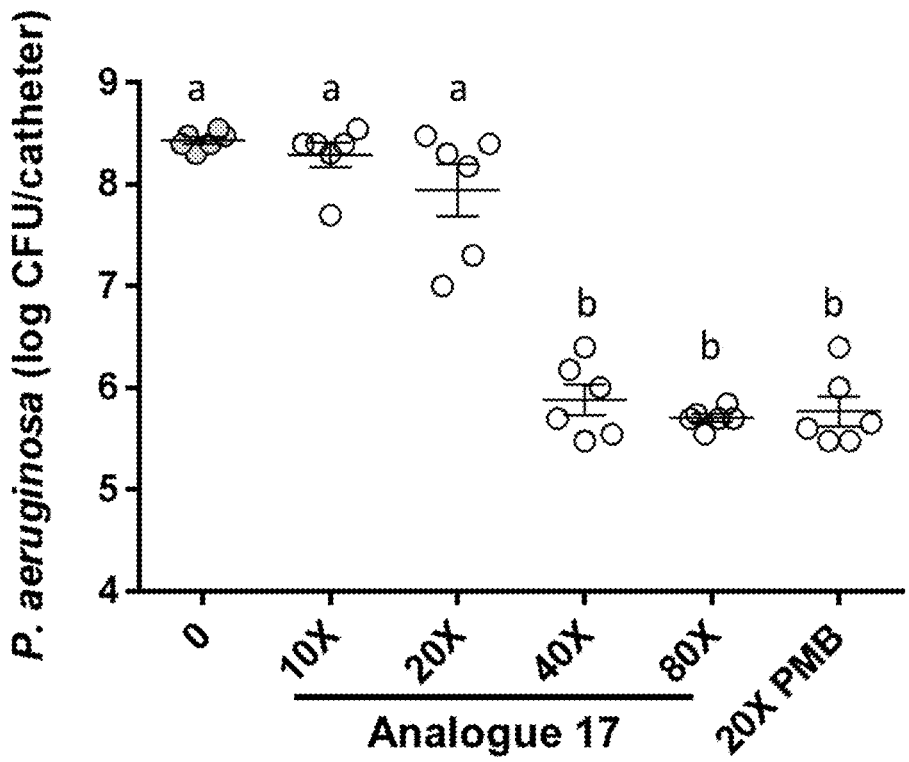

Bacterial cells in biofilms are more tolerant than planktonic cells to antibiotic treatment, thus making it important to identify those antibiotics that have the greatest efficacy in the context of an established biofilm. Previous studies demonstrated that daptomycin and ceftaroline are more active in this context than many other antibiotics. For this reason, evaluation of analogue 17 in the context of an established biofilm was based on comparison to these two antibiotics. As shown in FIG. 2A, the activity of analogue 17 was comparable to both of these antibiotics when tested in vitro in the context of established catheter-associated biofilm formed by the methicillin-resistant *S. aureus* strain LAC. Specifically, treatment with analogue 17 at 40 µg/mL (5×MIC) or 160 µg/mL (20×MIC) resulted in 3 log and 5 log reductions, respectively, of viable biofilm-associated *S. aureus* cells. Moreover, at a concentration equal to 20 times its MIC, exposure to analogue 17 completely cleared three of six catheters of viable bacteria (50%), whereas exposure to daptomycin at an equivalent multiple of its MIC only cleared one of six catheters (17%), and none were cleared by an equivalent concentration of ceftaroline. Analogue 12, which had the lowest MIC as assessed using planktonic cells of the *S. aureus* strain LAC, had no activity in the context of an established catheter-associated biofilm (data not shown). Analogue 17 was also tested against biofilms formed by *P. aeruginosa* ATCC 27853 using the same in vitro catheter-associated biofilm model. After exposure to analogue 17 at 40× MIC (40 µg/ml), a 2.6 log reduction was observed in the number of viable *P. aeruginosa* cells in an established biofilm (FIG. 2B).

Potentiation of Gram-Negative Pathogens to Rifampicin and Clarithromycin

Gram-negative bacteria, including *Acinetobacter* and *Klebsiella*, are intrinsically resistant to the hydrophobic antibiotic rifampicin. The MIC of rifampicin against *A. baumannii* ATCC 19606 and *K. pneumoniae* ATCC 13883 was 16 µg/mL (Table 11). Ten paenipeptin analogues, which were devoid of direct antibacterial activity against *Acinetobacter* and *Klebsiella* when used alone, were investigated for a potential synergistic effect with rifampicin. Paenipeptin analogue 13 was the only tested compound that did not show synergism with rifampicin. This is likely due to the replacement of the positively-charged Dab with Thr at position 3 in the peptide. This substitution reduces the overall charges of the peptide and thus may decrease the interaction with LPS in Gram-negative bacteria. Therefore, analogue 13 may not be able to promote the entry of rifampicin into Gram-negative pathogens. Nine analogues displayed various degrees of synergistic effects with rifampicin. When tested at 4 µg/mL, six paenipeptin analogues (1, 3, 9, 14, 15 and 16) decreased the MICs of rifampicin against both *Acinetobacter* and *Klebsiella* from 16 µg/mL to a range between <0.00098 µg/mL and 0.0078 µg/mL, which corresponded to a 2,048 to 8,192-fold increase in the antibacterial activity of rifampicin (Table 11).

TABLE 11

Minimum inhibitory concentration (MIC) of rifampicin with or without paenipeptin analogues
MIC of rifampicin (µg/ml) at the following concentrations of paenipeptin analogues

| | Acinetobacter baumannii ATCC 19606 | | | | Klebsiella pneumoniae ATCC 13883 | | | |
|---|---|---|---|---|---|---|---|---|
| An. | 0 µg/mL | 2 µg/mL | 4 µg/mL | Sensitization factor [a] | 0 µg/mL | 2 µg/mL | 4 µg/mL | Sensitization factor |
| 1 | 16 | 0.0078-0.0156 | 0.00195-0.0039 | 4,096-8,192 | 16 | 0.0039 | 0.00195 | 8,192 |
| 2 | 16 | 0.125 | 0.0313-0.0625 | 256-512 | 16 | 0.0156 | 0.0039 | 4,096 |
| 3 | 16 | 0.0078 | 0.0039 | 4,096 | 16 | 0.0039 | <0.00098-0.00195 | ≥8,192 |
| 9 | 16 | 0.0019 | 0.00195 | 8,192 | 16 | 0.0019-0.0039 | <0.00098-0.00195 | ≥8,192 |
| 10 | 16 | 0.03125-0.0625 | 0.0313-0.0625 | 256-512 | 16 | 0.0625-0.125 | 0.0625 | 256 |
| 11 | 16 | 0.0625 | 0.0156-0.0313 | 512-1,024 | 16 | 0.0313-0.0625 | 0.0078-0.0156 | 1,024-2,048 |
| 13 | 16 | >0.125 | >0.125 | <128 | 16 | >0.125 | >2 | <8 |
| 14 | 16 | 0.03125 | 0.0039-0.0078 | 2,048-4,096 | 16 | 0.0078 | 0.00195-0.0039 | 4,096-8,192 |
| 15 | 16 | 0.0019-0.0039 | <0.00098-0.00195 | ≥8,192 | 16 | 0.0039 | 0.00195-0.0039 | 4,096-8,192 |
| 16 | 16 | 0.0039-0.0078 | 0.0039 | 4,096 | 16 | 0.0039 | <0.00098-0.00195 | ≥8,192 |

[a] Sensitization factor: the ratio of the MIC in the absence of paenipeptins to that in the presence of 4 µg/mL of paenipeptins.

Two paenipeptin analogues (9 and 16) that showed promising synergism with rifampicin were selected for further testing in combination with four additional antibiotics that have different mechanisms of action. Specifically, clarithromycin and erythromycin block protein synthesis whereas vancomycin and ampicillin inhibit cell wall biosynthesis. These four antibiotics when used alone were not effective against Gram-negative pathogens (MIC≥32 µg/ml). When combined with analogues 9 and 16 at 4 µg/ml, clarithromycin showed a 2,048 to 8,192-fold increase in its activity against A. baumannii ATCC 19606 and K. pneumoniae ATCC 13883 (Table 12). In the presence of analogues 9 and 16 at 4 µg/ml, erythromycin exhibited a moderate increase (64 to 512-fold) against these two pathogens. Interestingly, analogues 9 and 16 potentiated the activity of vancomycin against A. baumannii but not K. pneumoniae. No synergistic effect was observed between analogues 9 or 16 and ampicillin (Table 12).

For studies with LPS, P. aeruginosa ATCC 27853 was diluted with TSB to contain approximately $10^6$ CFU/mL. LPS purified from E. coli O111:B4 (Sigma) was added to the cell suspension at a final concentration of 10, 25, 50, or 100 µg/mL. This was followed by adding paenipeptin analogue 17 to a final concentration of 16 µg/mL. The mixtures were incubated at 37° C. with agitation at 200 rpm for 60 min. Surviving cells were quantified by plating on TSA. There were three independent experiments with one replicate in each experiment. For experiments with LTA, S. aureus ATCC 29213 was diluted to ~$10^6$ CFU/mL and mixed with LTA (Sigma) isolated from S. aureus at a final concentration of 10, 25, 50, or 100 µg/mL. After adding analogue 17 at a final concentration of 32 µg/mL and incubating at 37° C. with agitation at 200 rpm for 60 min, surviving S. aureus cells were enumerated by plating on TSA. There were four independent experiments with one replicate in each experiment.

TABLE 12

Minimum inhibitory concentration (MIC) of ampicillin, clarithromycin, erythromycin and
vancomycin with or without paenipeptin analogues 9 and 16
MIC (µg/ml) of antibiotics in the presence of 0 or 4 µg/ml paenipeptin analogues

| | | Acinetobacter baumannii ATCC 19606 | | | Klebsiella pneumoniae ATCC 13883 | | |
|---|---|---|---|---|---|---|---|
| Analogue | | 0 µg/ml | 4 µg/ml | Sensitization factor[a] | 0 µg/ml | 4 µg/ml | Sensitization factor |
| 9 | Ampicillin | >32 | 1-2 | 16-32 | 32 | 32 | 1 |
| | Clarithromycin | 32 | 0.0039-0.0078 | 4,096-8,192 | 32 | 0.0156 | 2,048 |
| | Erythromycin | 32 | 0.125-0.25 | 128-256 | >32 | 0.0625 | 512 |
| | Vancomycin | >32 | 0.25-0.5 | 64-128 | >32 | 16 | 2 |
| 16 | Ampicillin | >32 | 8-16 | 2-4 | 32 | 32 | 1 |
| | Clarithromycin | 32 | 0.0156 | 2,048 | 32 | 0.0078-0.0156 | 2,048-4,096 |
| | Erythromycin | 32 | 0.5 | 64 | >32 | 0.0625 | 512 |
| | Vancomycin | >32 | 0.5-1 | 32-64 | >32 | >32 | 1 |

[a] Sensitization factor: the ratio of the MIC in the absence of paenipeptins to that in the presence of 4 µg/mL of paenipeptins Interaction of Paenipeptin Analogues with Lipopolysaccharides and Lipoteichoic Acid To identify the initial binding target of paenipeptin on the cell surface, purified LPS or LTA were investigated for their impact on bactericidal activities of paenipeptin analogue 17.

Figure 3A:
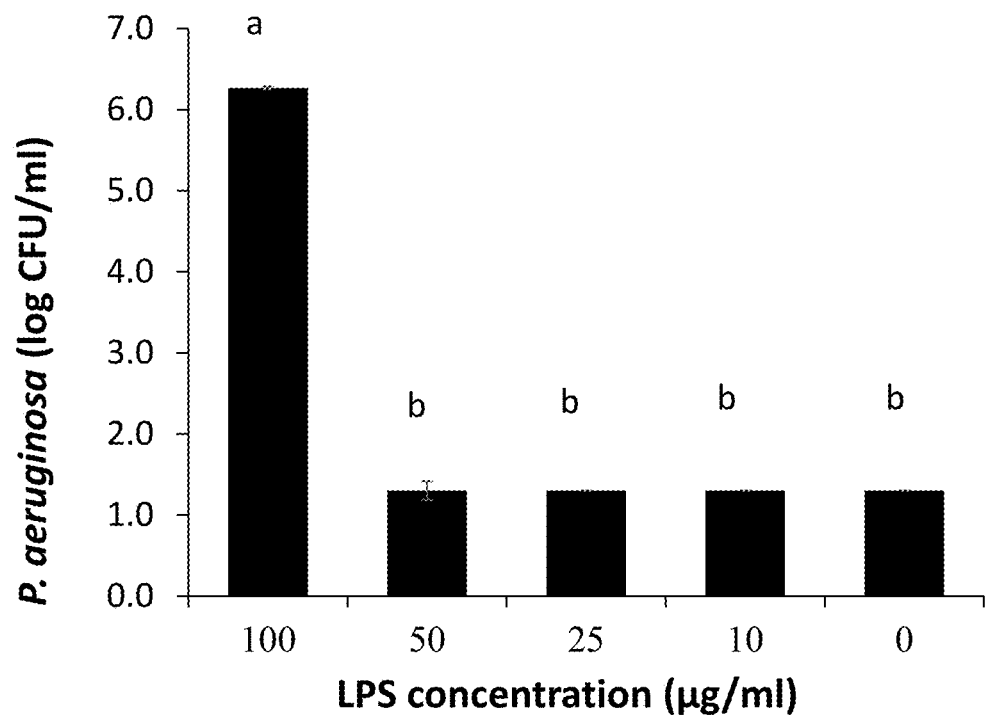
FIGS. 3A-3B shows the impact of lipopolysaccharide (LPS) and lipoteichoic acid (LTA) on antimicrobial activity of paenipeptin analogue 17.
Figure 3B:
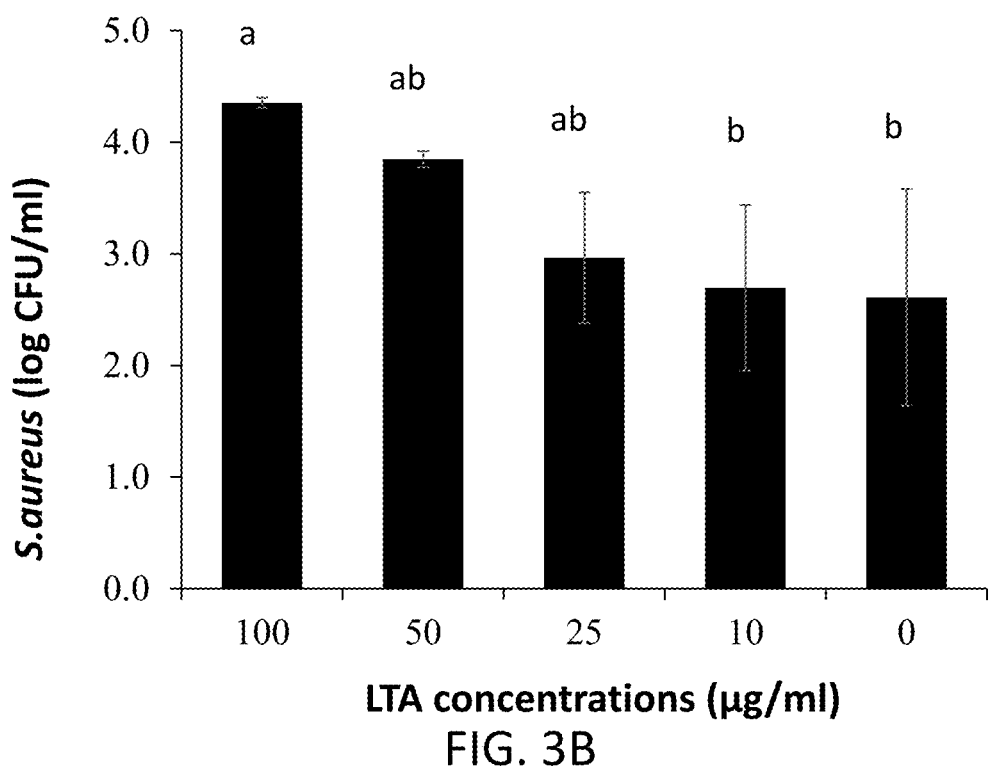

Purified LPS had a significant impact on the antimicrobial activity of paenipeptin analogue 17 against P. aeruginosa ATCC 27853. The addition of purified LPS at a high concentration (100 µg/ml) neutralized the bactericidal activity of 17 (FIG. 3A). A similar trend was observed for analogues 7, 8, 9, and 12 (data not shown). These results suggest that paenipeptin has a high affinity for LPS from the outer membrane of Gram-negative bacteria. Therefore, LPS on the Gram-negative cell surface is likely the initial binding target of paenipeptin. In Gram-positive bacteria, negatively charged lipoteichoic acids (LTA) are an important component on the cell surface. As shown in FIG. 3B, at 100 µg/mL, purified LTA significantly reduced the antibacterial activity of analogue 17 against S. aureus ATCC 29213. LTA at 50 µg/ml showed some inhibition, but the effect was not statistically different from the control without LTA. These results suggest that LTA in Gram-positive bacteria may also serve as a docking molecule for paenipeptins, likely through electrostatic interactions. This is consistent with the observation that negatively-charged LTA was reported as the initial target of several cationic peptides, including nisin and brevibacillin.

Cytoplasmic Membrane Integrity Assay

The disturbance of membrane potential after paenipeptin treatment was determined using the fluorescent probe 3,3'-dipropylthiadicarbocyanine iodide [DiSC$_3$(5); Invitrogen]. DiSC$_3$(5) is membrane potential-sensitive dye, which accumulates in polarized cytoplasmic membranes and becomes self-quenched. For each assay, an overnight culture of P. aeruginosa ATCC 27853 or S. aureus ATCC 29213 was diluted 1/100 in TSB and grown at 37° C. with agitation at 200 rpm for ~5 h. After incubation, bacterial cells were harvested by centrifugation at 3,660×g at 4° C. for 10 min and washed twice using 5 mM HEPES buffer (pH 7.2, Sigma) supplemented with 5 mM glucose (buffer A). Cells of S. aureus were resuspended in buffer A, while P. aeruginosa cells were resuspended in buffer B (buffer A supplemented with 0.2 mM EDTA), which is known to promote the uptake of DiSC$_3$(5) by Gram-negative bacteria. DiSC$_3$(5) was added to the cell suspensions at a final concentration of 0.5 µM, followed by incubation for 15 min at room temperature. After incubation, KCl was added at a final concentration of 100 mM. Aliquots (90 µL) of the cell suspension with integrated DiSC$_3$(5) were added to wells of a black NBS microplate (Corning Inc.). This was followed by adding 10 µL of paenipeptin analogue 17 at a final concentration of 8-64 µg/mL. The increase of fluorescence signal due to membrane depolarization and release of the DiSC$_3$(5) probe from bacterial cells was recorded using a Cell Imaging Multimode Reader (Cytation 3, BioTek) at an excitation of 622 nm and an emission of 670 nm. There were three independent experiments with one replicate in each experiment.

Potassium Ion Release Assay

Potassium ions leaked from paenipeptin treated bacterial cells were measured using a K$^+$-sensitive probe (PBFI; Invitrogen), which is impermeable to healthy bacterial cells. Cell suspensions of S. aureus ATCC 29213 and P. aeruginosa ATCC 27853 were prepared in buffer A using the same procedures aforementioned in the cytoplasmic membrane integrity assay. Aliquots (90 µL) of bacterial cells were dispensed to wells of a black NBS microplate. The PBFI K$^+$-sensitive probe was added to the cell suspension at a final concentration of 2 µM. This was followed by adding 10 µL of paenipeptin analogue 17 at a final concentration of 8-64 µg/mL. A change in fluorescence corresponding to potassium ion concentration in the buffer was recorded using a Cell Imaging Multimode Reader (Cytation 3, BioTek) at an excitation wavelength of 346 nm and an emission wavelength of 505 nm. There were three independent experiments with one replicate in each experiment.

Figure 4A:
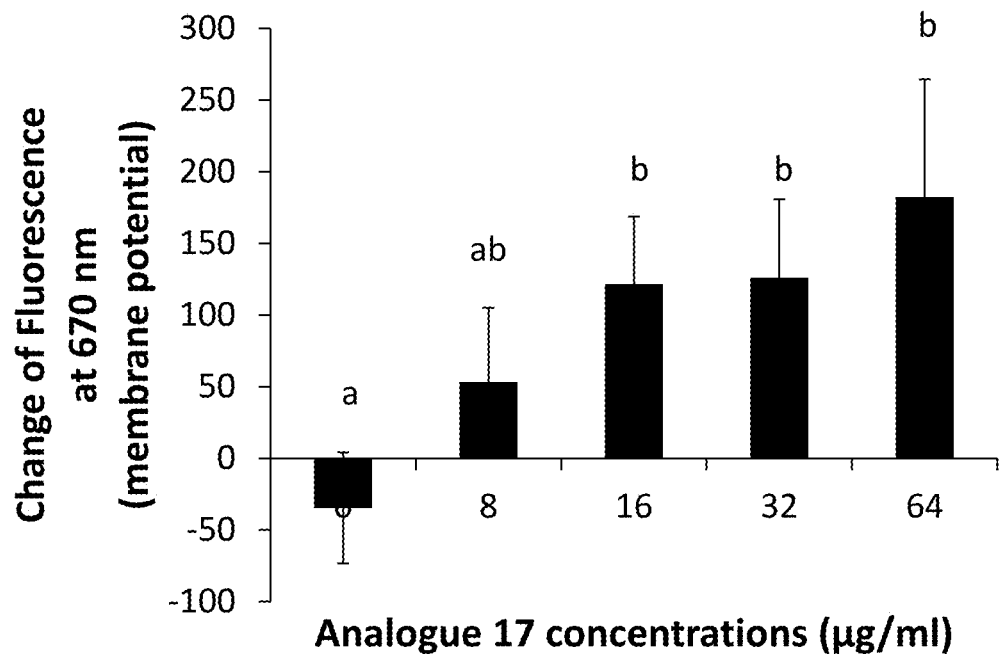
FIGS. 4A-4B show changes in bacterial membrane potential in the presence of paenipeptin analogue 17.
Figure 4B:
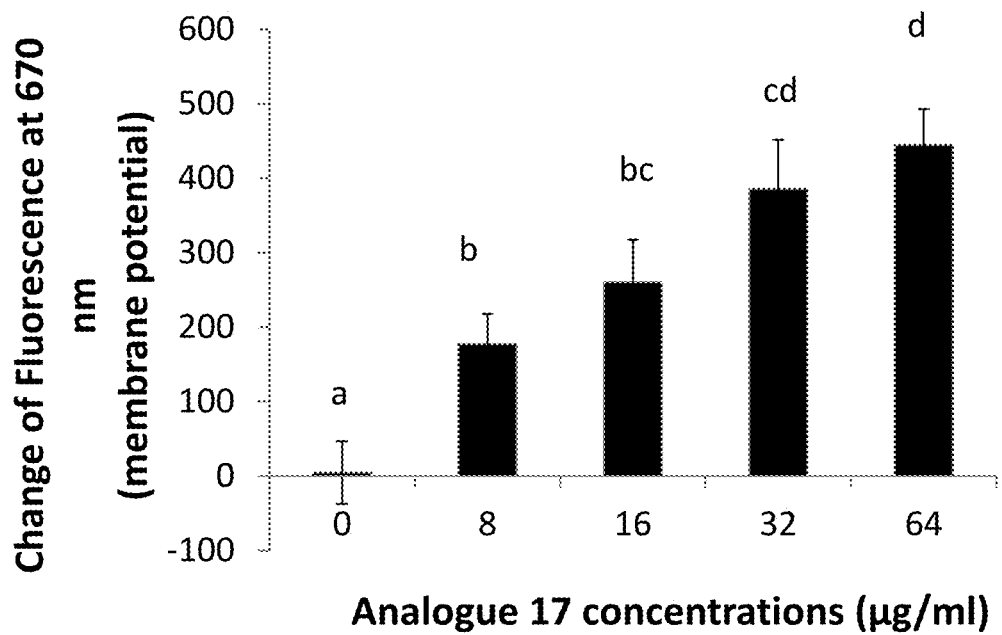
Figure 5A:
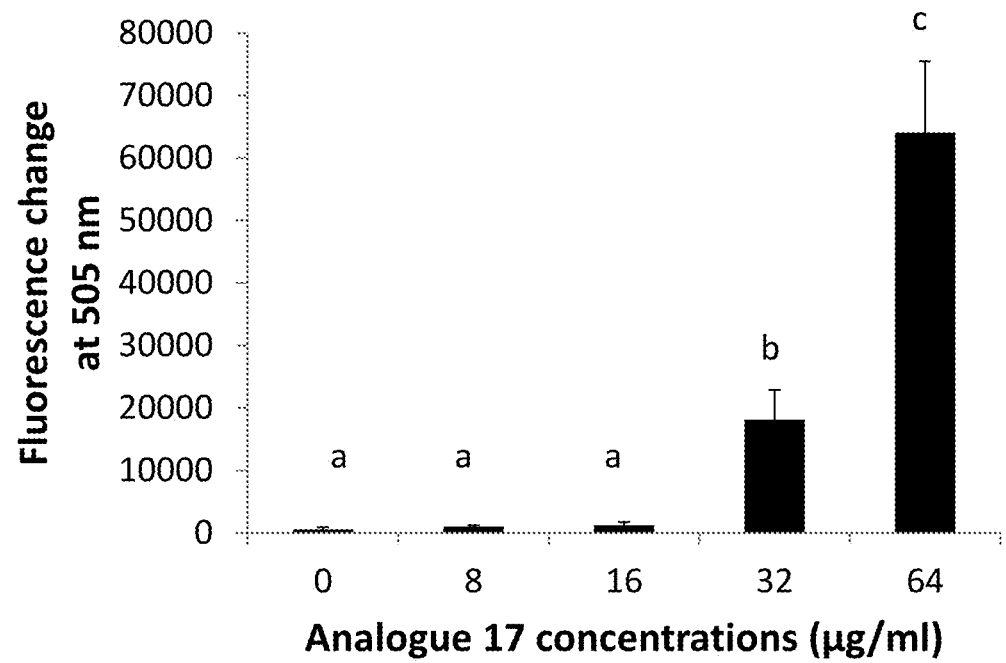
FIGS. 5A-5B show release of intracellular potassium ions from bacterial cells in the presence of paenipeptin analogue 17.
Figure 5B:
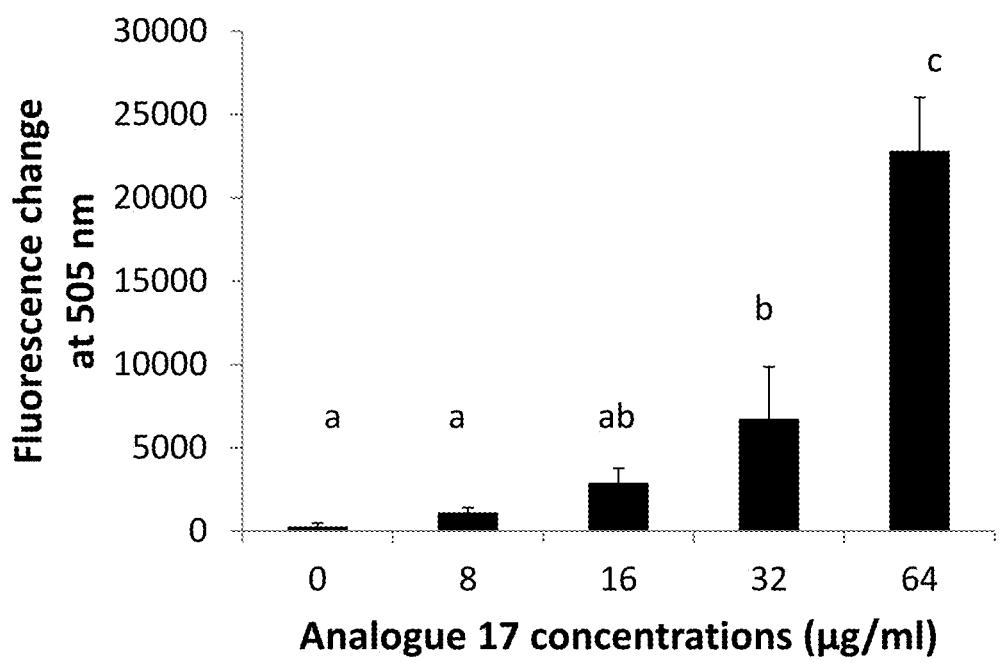

Bacterial cells maintain a proton gradient across the cytoplasmic membrane where electrical potential gradient is a main component of the proton motive force. As shown in FIGS. 4A-4B, paenipeptin analogue 17 at ≥16 µg/mL depolarized the membrane potential as evidenced by the increase of fluorescence due to the release of a DiSC$_3$(5) probe, which is only accumulated in healthy, polarized cell membranes. Moreover, analogue 17 at 32-64 µg/mL significantly released intracellular potassium ions from treated P. aeruginosa and S. aureus cells (FIGS. 5A-5B). Therefore, the bactericidal activity of paenipeptins can likely be attributed to disruption and damage of the cytoplasmic membranes.

Statistical Analysis

For bacterial inactivation assays, the surviving cell counts at the end of each experiment were analyzed. For fluorescence measurements, the changes in fluorescence strength before and after adding analogue 17 were analyzed. All data were subjected to analysis of variance (ANOVA) followed by Tukey's honest significant difference (HSD) tests using SPSS Statistics (version 24; SPSS, Inc., Chicago, Ill., USA).

Potentiation of Clarithromycin and Rifampicin against Carbapenem-Resistant Pathogens Through structure-activity relationship (SAR) studies above, we identified two analogues (1 and 15), which are nonhemolytic at 128 µg/ml. Paenipeptin analogue 1 possesses a shorter lipid chain (C6) in comparison with paenipeptin C', whereas analogue 15 substitutes the lipid chain with a hydrophobic carboxybenzyl group. These two analogues potentiated rifampicin against two reference stains, Acinetobacter baumannii ATCC 19606 and Klebsiella pneumoniae ATCC 13883. The cationic nature of paenipeptin analogues may disrupt the outer membrane of Gram-negative pathogens, which promotes the entry of hydrophobic antibiotics to attack the intracellular drug targets. In this study, we aimed to evaluate the cytotoxicity of paenipeptin analogues (1 and 15) and determined the potential potentiation with clarithromycin or rifampicin against 10 carbapenem-resistant strains, including Acinetobacter baumannii and Klebsiella pneumoniae from the FDA-CDC Antimicrobial Resistance Isolate Bank.

The minimum inhibitory concentration (MIC) of clarithromycin (a protein synthesis inhibitor), rifampicin (an RNA synthesis inhibitor), polymyxin B nonapeptide, paenipeptin analogues or their combinations was determined against 10 carbapenem-resistant strains using a microdilution method. Paenipeptin analogue 1 or 15 alone showed inhibitory activity against certain A. baumannii isolates, such as AR 0037, AR 0052, AR 0063, and AR 0070, which were also susceptible to rifampicin (Table 13). The increased susceptibility of these isolates could be strain dependent with a higher rate in A. baumannii; none of the five tested K. pneumoniae strains was susceptible to paenipeptin or rifampicin. Paenipeptins 1 and 15 showed similar MIC in the presence of 10% fetal bovine serum (FBS), which was used in the tissue culture experiments for cytotoxicity assays. Polymyxin B nonapeptide, which is known as an antibiotic potentiator, was not effective against all 10 tested strains (MIC>32 µg/ml) when used alone (Table 13). As showed in Table 14, the combination of polymyxin B nonapeptide with clarithromycin or rifampicin showed a moderate potentiation effect when compared to paenipeptin analogues. In contrast, paenipeptin analogues dramatically increased the antibacterial activity of clarithromycin and rifampicin. For example, paenipeptin analogues 1 and 15 at 4 µg/mL decreased the MIC of clarithromycin against A. baumannii FDA-CDC AR 0037 from 16 µg/ml to 0.0313 and 0.0019 µg/ml, respectively, which corresponded to 512 to 8192-fold increase in its antibiotic activity (Table 14). These results were consistent with our previous findings where paenipeptin analogues increased the efficacy of antibiotics against antibiotic-susceptible reference strains.

TABLE 13

Minimum inhibitory concentration (MIC) of clarithromycin, rifampicin, polymyxin B nonapeptide, paenipeptin analogues 1 and 15 against 10 carbapenem-resistant pathogens from the FDA-CDC Antimicrobial Resistance Isolate Bank

| | MIC (µg/ml) | | | | | | |
|---|---|---|---|---|---|---|---|
| Antibiotic-resistant | | | polymyxin B | analogue 1 | | analogue 15 | |
| clinical isolates | clarithromycin | rifampicin | nonapeptide | No FBS[a] | 10% FBS | No FBS | 10% FBS |
| *A. baumannii* | | | | | | | |
| FDA-CDC AR 0037 | 16 | 2 | >32 | 8 | 16 | 8 | 4 |
| FDA-CDC AR 0052 | 4 | 1 | >32 | 2-4 | 2-4 | ≤0.5 | <0.5 |
| FDA-CDC AR 0063 | 16-32 | 1 | >32 | 8-32 | 32 | 0.5-4 | 2 |
| FDA-CDC AR 0070 | 2-4 | 1 | >32 | 2 | 2-8 | ≤0.5 | 0.5-1 |
| FDA-CDC AR 0083 | >32 | 32 | >32 | 32 | ≥32 | 8-16 | 4-8 |
| *K. pneumoniae* | | | | | | | |
| FDA-CDC AR 0034 | >32 | 16 | >32 | ≥32 | >32 | ≥32 | >32 |
| FDA-CDC AR 0044 | >32 | 32 | >32 | 16 | 16 | 32 | 16-32 |
| FDA-CDC AR 0068 | >32 | 32 | >32 | >32 | >32 | >32 | >32 |
| FDA-CDC AR 0080 | >32 | >32 | >32 | 16 | 32 | 32 | 32 |
| FDA-CDC AR 0097 | >32 | 32 | >32 | >32 | 16-32 | >32 | 16-32 |

[a]FBS: fetal bovine serum; the MIC of paenipeptin analogues 1 and 15 was tested with or without 10% FBS.

TABLE 14

Minimum inhibitory concentration (MIC, µg/ml) of clarithromycin and rifampicin in combination with polymyxin B nonapeptide (PMBN), paenipeptin analogues 1, or analogue 15 against 10 carbapenem-resistant pathogens from the FDA-CDC Antimicrobial Resistance Isolate Bank

| | MIC of clarithromycin and rifampicin at the presence of PMBN or paenipeptin analogue at 4 µg/ml | | | | | |
|---|---|---|---|---|---|---|
| Antibiotic-resistant clinical isolates | Clarithromycin + PMBN | clarithromycin + analogue 1 | clarithromycin + analogue 15 | rifampicin + PMBN | rifampicin + analogue 1 | rifampicin + analogue 15 |
| *A. baumannii* | | | | | | |
| FDA-CDC AR 0037 | 0.125-0.25 | 0.0313 | ≤0.0019 | 0.25 | 0.0039 | ≤0.0019 |
| FDA-CDC AR 0052 | 0.0313-0.0625 | —[a] | — | 0.0625-0.125 | — | — |
| FDA-CDC AR 0063 | 0.5-1 | 0.0313 | — | 0.125 | ≤0.0019 | — |
| FDA-CDC AR 0070 | 0.25-0.5 | — | — | 0.0625-0.125 | — | — |
| FDA-CDC AR 0083 | 32 | 16 | 1-4 | 8 | 0.25-0.5 | 0.0313-0.0625 |
| *K. pneumoniae* | | | | | | |
| FDA-CDC AR 0034 | >32 | 0.25 | 0.125-0.5 | 1 | ≤0.0019 | ≤0.0019 |
| FDA-CDC AR 0044 | 4 | 0.0156 | 0.0078-0.0156 | 2 | ≤0.0019 | ≤0.0019 |
| FDA-CDC AR 0068 | >32 | 1 | >32 | 2-8 | 0.0039-0.0156 | 0.0039-0.0078 |
| FDA-CDC AR 0080 | 4 | 0.0313 | 0.0156 | >32 | 0.0625 | 0.0313 |
| FDA-CDC AR 0097 | 32 | 0.0313-0.0625 | 0.0078-0.0156 | 16 | 0.0039-0.0078 | 0.0019-0.0039 |

Figure 6A:
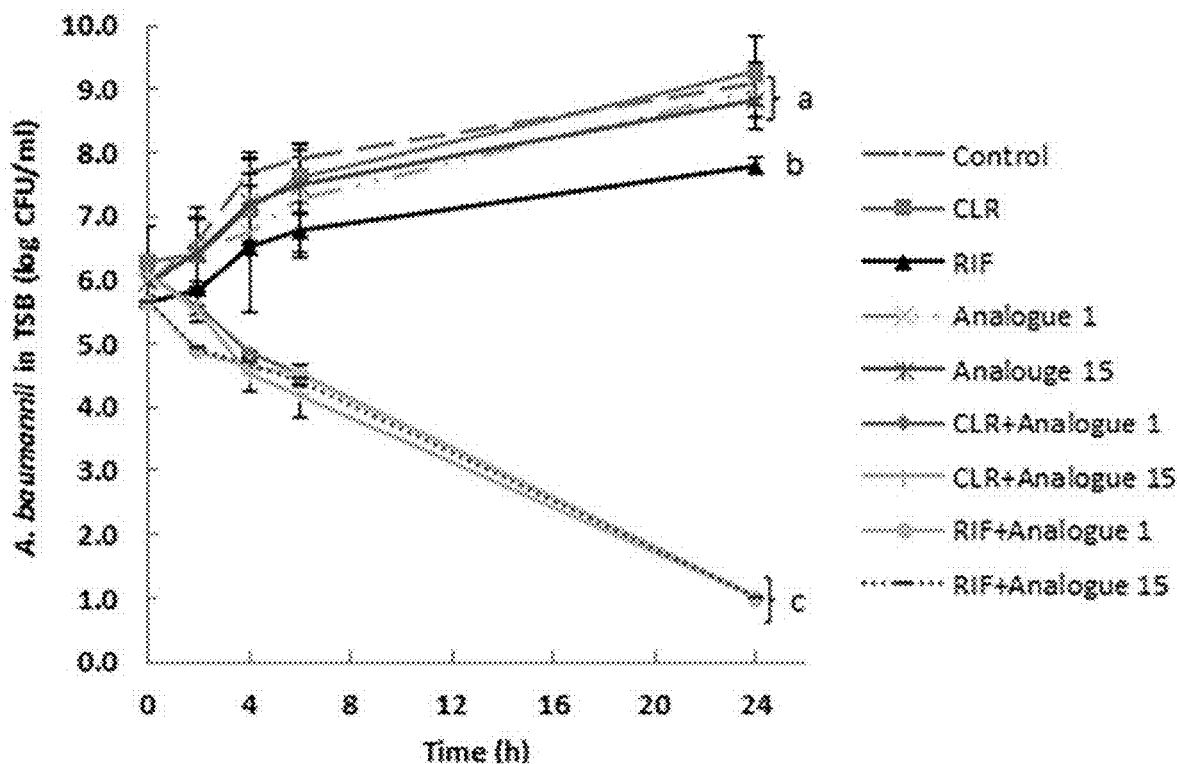
FIGS. 6A-6B show time-kill curves of carbapenem-resistant pathogens with exposure to analogue 1 or 15 alone at 4 µg/ml and in combination with clarithromycin (CLR) or rifampicin (RIF) at 1 µg/ml in tryptic soy broth (TSB).
Figure 6B:
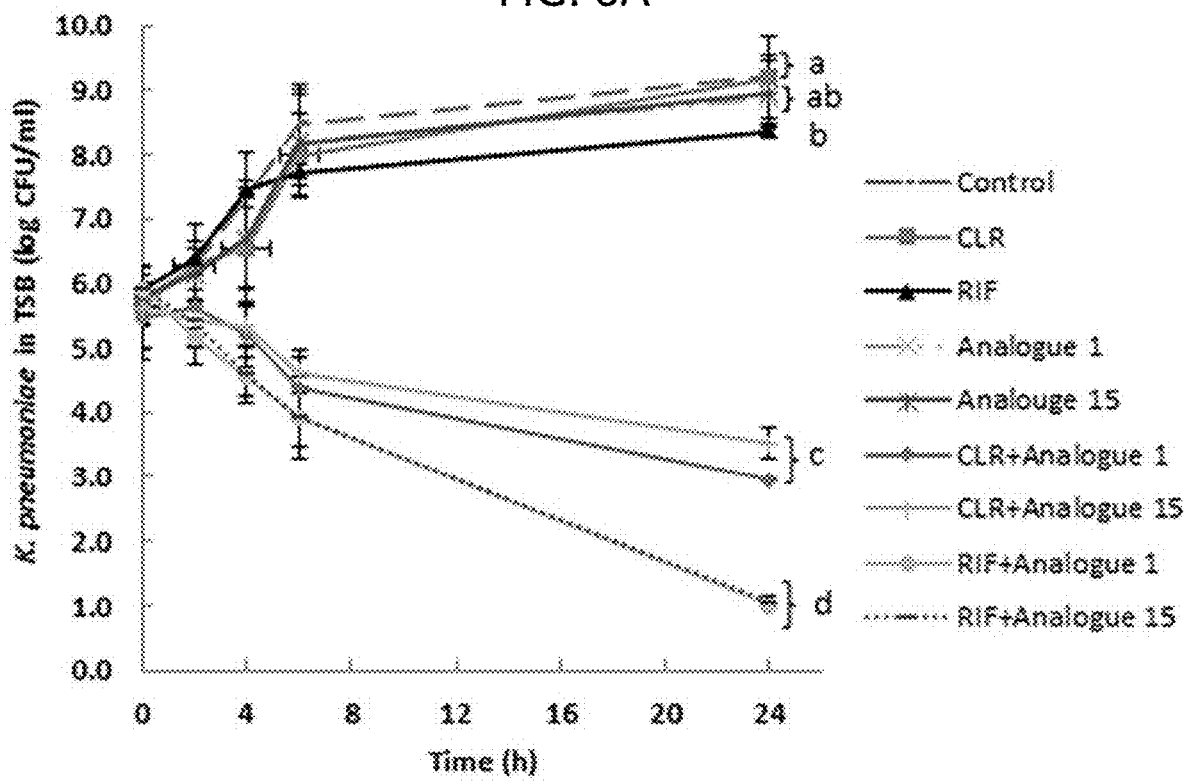

[a]not tested because of no bacterial growth at the presence of paenipeptin analogues 1 or 15 alone at 4 µg/m Time-kill kinetics assays were used to determine the bacteriostatic or bactericidal activity of clarithromycin or rifampicin in the presence of paenipeptin analogues. Paenipeptin analogues, clarithromycin, and rifampin were used at therapeutically-relevant concentrations in the time-kill kinetics assays. Bacterial viable counts were determined at 0, 2, 4, 6, and 24 h after antimicrobial treatment. Bacterial surviving counts at 24 h endpoints were subjected to analysis of variance (ANOVA) followed by Tukey's honest significant difference (HSD) tests using SPSS Statistics (version 24; SPSS, Inc., Chicago, Ill., USA). As shown in FIG. 6A, when used alone, paenipeptin analogues at 4 µg/ml and clarithromycin or rifampicin at 1 µg/ml didn't inhibit the growth of *A. baumannii* FDA-CDC AR 0063 in tryptic soy broth at 37° C.; the bacterial population increased 2.1-3.0 log within 24 h. Conversely, the cell population steadily declined over time when treated by paenipeptin analogue 1 or 15 in combination with clarithromycin or rifampicin. The combined treatment resulted in 4.7-5.1 log reduction within 24 h. A similar trend was observed for a second carbapenem-resistant pathogen, *K. pneumoniae* FDA-CDC AR 0097 (FIG. 6B). Paenipeptin analogues, clarithromycin or rifampicin alone was not bactericidal at tested concentrations against *K. pneumoniae* FDA-CDC AR 0097; the combination of paenipeptin analogues with clarithromycin reduced the cell counts by 2.1-2.5 log in 24 h while the combination with rifampicin produced 4.9 log reduction within 24 h in tryptic soy broth (FIG. 6B). Therefore, paenipeptin analogues plus clarithromycin or rifampicin were significantly superior to either single agent against both *A. baumannii* and *K. pneumoniae* in tryptic soy broth.

Figure 7A:
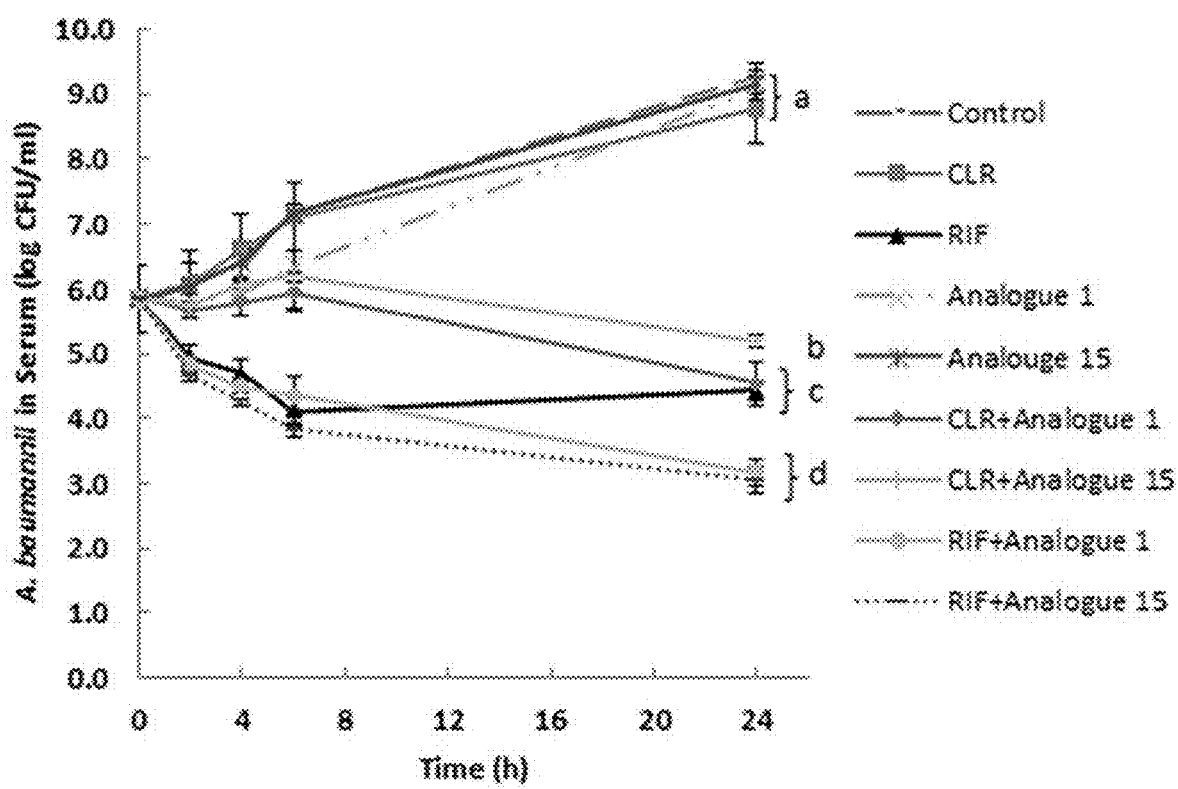
FIGS. 7A-7B show time-kill curves of carbapenem-resistant pathogens with exposure to analogue 1 or 15 alone at 4 µg/ml and in combination with clarithromycin (CLR) or rifampicin (RIF) at 4 µg/ml in 95% human serum in vitro.

To further test the therapeutic potential of paenipeptin analogues, the time-kill kinetics assays of paenipeptins alone or in combination with other antibiotics were performed in 95% human serum in vitro. Without antimicrobial treatment, the population of *A. baumannii* FDA-CDC AR 0063 increased from 5.8 log to 9.3 log within 24 h. Rifampicin at 4 µg/ml resulted in 1.4 log reduction of the cell population in 24 h but other single antibiotic treatment was not effective (FIG. 7A). Rifampicin alone also showed similar or slightly better activity when compared with the combined treatments between clarithromycin and paenipeptin analogue 1 or 15. Moreover, the combination of rifampicin with paenipeptin analogue 1 or 15 decreased the bacterial population by 2.7 log, which was significantly better than each single agent treatment. Similarly, paenipeptin analogue 1 and 15 significantly potentiated clarithromycin against *A. baumannii* FDA-CDC AR 0063, leading to 1.3 and 0.7 log reduction respectively in 24 h in 95% human serum. (FIG. 7A).

Figure 7B:
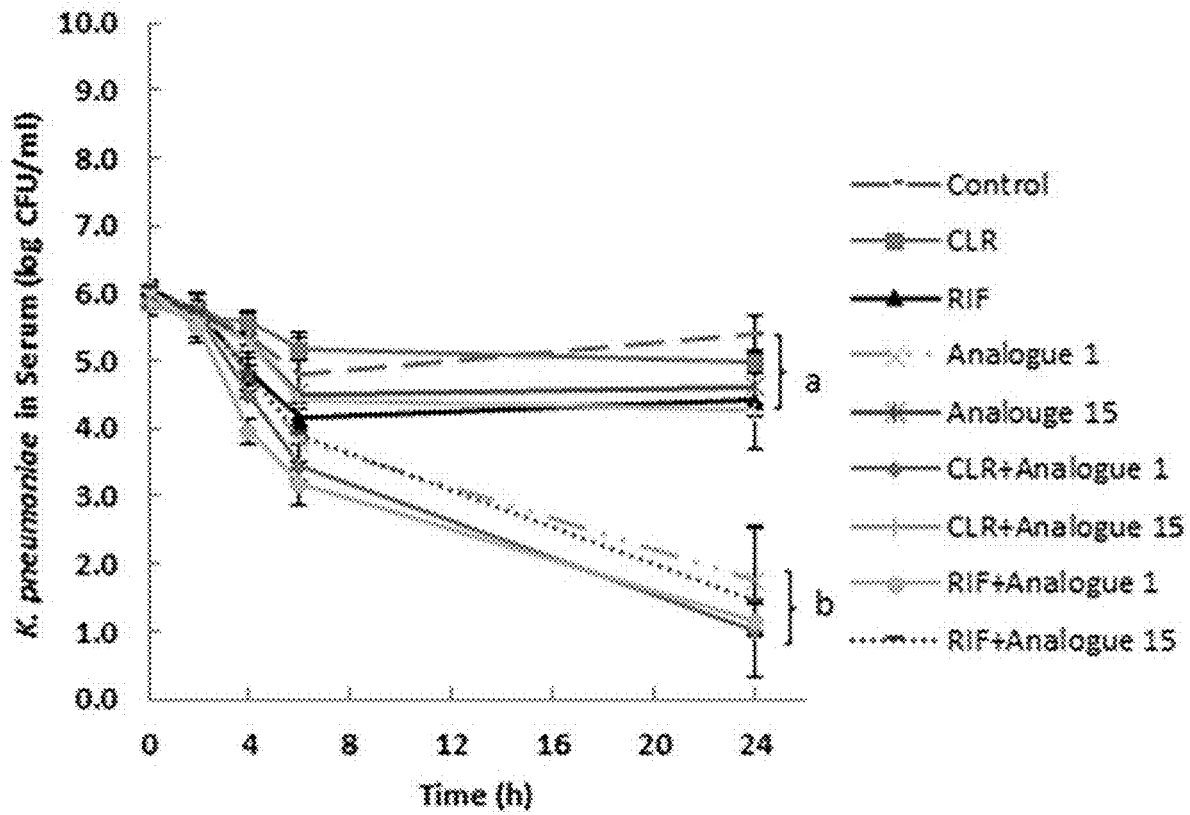

Human serum exhibited a bacteriostatic effect against *K. pneumoniae* FDA-CDC AR0097; the bacterial cell counts over 24 never exceed the initial bacterial population. We also observed that human serum inhibited the growth of a reference strain, *K. pneumoniae* ATCC 13883 (data not shown). Similarly, other researchers reported the inhibitory effect of human serum against certain *K. pneumoniae* strains (7, 8). The presence of human serum enhanced the bactericidal efficacy of paenipeptin analogue 1, which inactivated 4.2 log of *K. pneumoniae* cells within 24 h (FIG. 7B). The combination of analogue 1 with clarithromycin or rifampicin resulted in 4.9 log reduction in bacterial population in 24 h, even though the combined treatment was not statistically better than analogue 1 alone in 95% human serum. Paenipeptin analogue 15, which differs from analogue 1 at the N-terminus, didn't show bactericidal activity nor potentiate clarithromycin against *K. pneumoniae* FDA-CDC AR0097 in human serum. However, when analogue 15 was combined with rifampicin, 4.6 log reduction was achieved within 24 h (FIG. 7B). Therefore, the combination between analogue 15 and rifampicin was significantly better than the respective single treatment against *K. pneumoniae* in 95% human serum.

---

The invention claimed is:

1. A compound comprising a peptide having at least 88% sequence identity with SEQ ID NO: 6 interposed between a terminus —$R^1$ and an amine terminus —$NR^2R^3$,
   wherein $R^1$ comprises a substituted or unsubstituted, branched or unbranched $C_2$-$C_{20}$ alkanoyl and
   wherein $R^2$ and $R^3$ are independently selected from hydrogen or a $C_1$-$C_6$ alkyl.

2. The compound of claim 1, wherein peptide comprises $R^1$—$X^1$—$X^2$—$X^3$—$X^4$—$X^5$—$X^6$—$X^7$—$X^8$—$X^9$—$NR^2R^3$ and
   $X^1$ is selected from the group consisting of Dab, Orn, Dap, Lys and Arg;
   $X^2$ is selected from the group consisting of Ile, Val, Phe, Dap, and Phephe;
   $X^3$ is selected from the group consisting of Dab, Orn, Dap, Thr, Lys and Arg;
   $X^4$ is selected from the group consisting of dLeu, dPhe, and Phephe;
   $X^5$ is selected from the group consisting of Leu, Phe and Phephe;
   $X^6$ is selected from the group consisting of Dab, Orn, Dap, Lys and Arg;
   $X^7$ is selected from the group consisting of dVal, dLeu, dPhe and Phephe;
   $X^8$ is selected from the group consisting of Leu, Phe, Phephe, and Octgly; and
   $X^9$ is selected from the group consisting of Ser and Dab.

3. The compound of claim 1, wherein the peptide is SEQ ID NO: 6.

4. The compound of claim 1, wherein —$R^1$ comprises:
   $R^4$—C(=O)— and $R^4$ is selected from the group consisting of alkyl, alkenyl, cycloalkyl, phenylalkyl, biphenylalkyl, alkylamine, cycloalkylamine, phenylalkylamine, biphenylalkylamine, alkoxy, cycloalkoxy, phenylalkoxy, or biphenphylalkoxy or $R^5$—CH($NH_2$)—C(=O)— and $R^5$ is selected from the group consisting of alkyl, alkenyl, cycloalkyl, phenylalkyl, and biphenylalkyl.

5. The compound of claim 1, wherein $R^2$ and $R^3$ are selected from hydrogen.

6. A composition comprising the compound of claim 1 and an antimicrobial agent.

7. The composition of claim 6, wherein
   (a) the antimicrobial agent has a minimum inhibitory concentration against a microbe in the presence of the compound less than a minimum inhibitory concentration against the microbe in the absence of the compound in a culture medium;
   (b) the antimicrobial agent has a minimum bactericidal concentration against a microbe in the presence of the compound less than a minimum bactericidal concentration against the microbe in the absence of the compound in a culture medium;
   (c) the composition has an effective amount of the compound and/or the antimicrobial agent for an antibiofilm activity of at least a 2.0 log reduction in viable microbes on a surface; or
   (d) any combination thereof.

8. A pharmaceutical composition comprising a therapeutically effective amount of the compound of claim 1 and a pharmaceutically acceptable excipient, a carrier, or a diluent.

9. A product comprising the compound of claim 1 formulated for application to a surface, wherein the surface is a medical device surface, a medical instrument surface, a medical implant surface, a bandage surface, a wound surface, or skin.

10. A bandage comprising a dressing and the compound of claim 1, wherein the dressing comprises a fabric, a sponge, an alginate, a collagen, a film, a gel sheet, a wound filler, a hydrogel, a hydrocolloid, or a combination thereof.

11. The compound according to claim 1, wherein the compound is

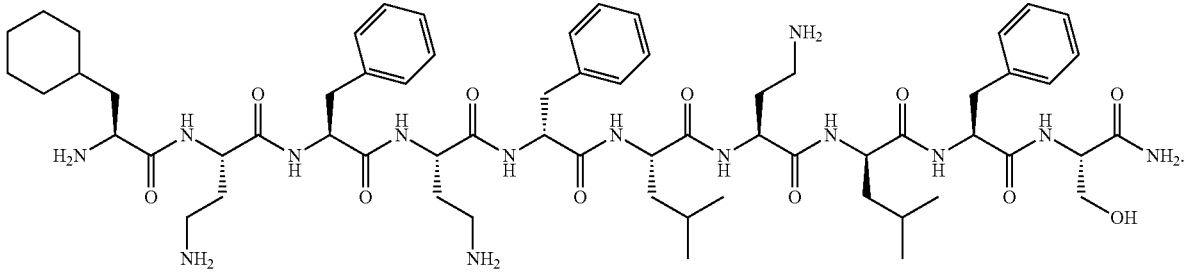 [SMILES: CC(C)C[C@H](NC(=O)[C@@H](Cc1ccccc1)NC(=O)[C@H](CCN)NC(=O)[C@H](Cc1ccccc1)NC(=O)[C@H](CCN)NC(=O)[C@@H](N)CC1CCCCC1)C(=O)N[C@@H](CCN)C(=O)N[C@H](CC(C)C)C(=O)N[C@@H](Cc1ccccc1)C(=O)N[C@@H](CO)C(N)=O]

* * * * *

UNITED STATES PATENT AND TRADEMARK OFFICE
CERTIFICATE OF CORRECTION

| | |
|---|---|
| PATENT NO. | : 11,364,275 B2 |
| APPLICATION NO. | : 16/635748 |
| DATED | : June 21, 2022 |
| INVENTOR(S) | : En Huang et al. |

It is certified that error appears in the above-identified patent and that said Letters Patent is hereby corrected as shown below:

In the Specification

Column 1, Line 13, insert the following section heading and paragraph:
--STATEMENT REGARDING FEDERALLY SPONSORED RESEARCH
This invention was made with government support under Grant Number W81XWH-15-1-0716, awarded by the Department of Defense Peer-Reviewed Orthopaedic Research Program. The government has certain rights in this invention.--

Signed and Sealed this
Twenty-sixth Day of December, 2023

Katherine Kelly Vidal
*Director of the United States Patent and Trademark Office*